US006287828B1

(12) United States Patent
Oriel et al.

(10) Patent No.: US 6,287,828 B1
(45) Date of Patent: Sep. 11, 2001

(54) METHOD FOR PRODUCING AMIDE COMPOUNDS USING A NITRILE HYDRATASE FROM A THERMOPHILIC BACILLUS

(75) Inventors: Patrick J. Oriel, Midland; Rugmini Padmakumar, East Lansing; Sang Hoon Kim, Okemos, all of MI (US)

(73) Assignee: Board of Trustees operating Michigan State University, East Lansing, MI (US)

( * ) Notice: Subject to any disclaimer, the term of this patent is extended or adjusted under 35 U.S.C. 154(b) by 0 days.

(21) Appl. No.: 09/550,394

(22) Filed: Apr. 14, 2000

Related U.S. Application Data

(62) Division of application No. 09/248,528, filed on Feb. 10, 1999, now Pat. No. 6,153,415
(60) Provisional application No. 60/083,485, filed on Apr. 29, 1998.

(51) Int. Cl.⁷ ....................................................... C12P 7/40
(52) U.S. Cl. .......................... 435/136; 435/227; 435/228; 435/252.5
(58) Field of Search ................................ 435/183, 252.3, 435/69.1, 136, 227, 228, 252.5

(56) References Cited

U.S. PATENT DOCUMENTS

| | | |
|---|---|---|
| 4,001,081 | 1/1977 | Commeyras et al. . |
| 4,248,968 | 2/1981 | Watanabe et al. . |
| 4,629,700 | 12/1986 | Prevatt et al. . |
| 4,637,982 | 1/1987 | Yamada et al. . |
| 5,130,235 | 7/1992 | Beppu et al. . |
| 5,135,858 | 8/1992 | Yamada et al. . |
| 5,334,519 | 8/1994 | Yamada et al. . |
| 5,563,053 | 10/1996 | Takashima et al. . |

OTHER PUBLICATIONS

Graham et al. Nitrile biotransformations using free and immobilized cells of a thermophilic *Bacillus* spp. Enzyme and Microbial Technology. Mar. 2000, vol. 26, pp. 368–373.*
Ashina, Y., et al., in Industrial Applications of Immobilized Biocatalysts, A. Tanaka, T. Tosa, T. Kobayashi, eds. Marcell Dekker, N.Y. p. 91–107 (1993).
Yamada; H., et al., Biosci. Biotech. Biochem. 60:1391–1400 (1996).
Cramp, R., et al., Microbiology 143:2313–2320 (1997).
Nagasawa, T., et al., Appl. Microbiol. Biotechnol. 40:189–195 (1993).
Maltseva, O., et al., Microbiology 142:1115–1122 (1996).
Rainey, F.A., et al., FEMS Microbiol. Lett. 115:205–212 (1994).
Payne, M.S., et al., Biochemisty 36:5447–5454 (1997).

* cited by examiner

*Primary Examiner*—Nashaat T. Nashed
*Assistant Examiner*—Christian L. Fronda
(74) *Attorney, Agent, or Firm*—Ian C. McLeod

(57) ABSTRACT

A process for the bioconversion of a nitrile to its corresponding amide product, particularly acrylonitrile to acrylamide which is used for forming polymers. The process uses a thermophilic bacterium having a nitrile hydratase activity that is constitutively expressed, activated by cobalt ions, stable at 60° C., and is most active between 20° C. to 70° C. with optimum activity at 55° C. Alternatively, the process uses the enzyme extracted from the thermophilic bacterium to convert a nitrile to its amide product. The genes encoding nitrile hydratase and amidase are described in which the former is useful for the conversion of an nitrile to its amide and the later is useful for the conversion of an amide to its acid.

6 Claims, 21 Drawing Sheets

```
ctcaggacga acgctggcgg cgtgcctaat acatgcaagt cgagcggacc gaagggagct   60
tgctccttta ggttagcggc ggacgggtga gtaacacgtg ggcaacctgc cctgcagact  120
gggataactt cgggaaaccg gagctaatac cggataacac cgaaaaccgc atggtttcg   180
gttgaaaggc ggcttttagc tgtcactgca ggatgggccc gcggcgcatt agctagttgg  240
tgaggtaacg gctcaccaag gcgacgatgc gtagccgacc tgagagggtg accggccaca  300
ctgggactga gacacggccc agactcctac gggaggcagc agtagggaat cttccgcaat  360
ggacgaaagt ctgacggagc aacgccgcgt gagcgaagaa ggtcttcgga tcgtaaagct  420
ctgttgtcag ggaagaacaa gtaccgttcg aacagggcgg tacctgacg gtacctgacg  480
aggaagccac ggctaactac                                              500
```

FIG. 6

Comparison of 16S rDNA sequences: BR vs. BS

BR: BR449 16S rDNA - 500 nt
Bsp: Bacillus sp. 16S rDNA - 500 nt scoring matrix: , gap penalties: -12/-2

100.0% identity;          Global alignment score: 2000

```
             10         20         30         40         50         60
BR   CTCAGGACGAACGCTGGCGGCGTGCCTAATACATGCAAGTCGAGCGGACCGAAGGGAGCT
     ::::::::::::::::::::::::::::::::::::::::::::::::::::::::::::
Bsp  CTCAGGACGAACGCTGGCGGCGTGCCTAATACATGCAAGTCGAGCGGACCGAAGGGAGCT
             10         20         30         40         50         60

70         80         90        100        110        120
BR   TGCTCCTTTAGGTTAGCGGCGGACGGGTGAGTAACACGTGGGCAACCTGCCCTGCAGACT
     ::::::::::::::::::::::::::::::::::::::::::::::::::::::::::::
Bsp  TGCTCCTTTAGGTTAGCGGCGGACGGGTGAGTAACACGTGGGCAACCTGCCCTGCAGACT
             70         80         90        100        110        120

130        140        150        160        170        180
BR   GGGATAACTTCGGGAAACCGGAGCTAATACCGGATAACACCGAAAACCGCATGGTTTTCG
     ::::::::::::::::::::::::::::::::::::::::::::::::::::::::::::
Bsp  GGGATAACTTCGGGAAACCGGAGCTAATACCGGATAACACCGAAAACCGCATGGTTTTCG
            130        140        150        160        170        180

190        200        210        220        230        240
BR   GTTGAAAGGCGGCTTTTAGCTGTCACTGCAGGATGGGCCCGCGGCGCATTAGCTAGTTGG
     ::::::::::::::::::::::::::::::::::::::::::::::::::::::::::::
Bsp  GTTGAAAGGCGGCTTTTAGCTGTCACTGCAGGATGGGCCCGCGGCGCATTAGCTAGTTGG
            190        200        210        220        230        240

250        260        270        280        290        300
BR   TGAGGTAACGGCTCACCAAGGCGACGATGCGTAGCCGACCTGAGAGGGTGACCGGCCACA
     ::::::::::::::::::::::::::::::::::::::::::::::::::::::::::::
Bsp  TGAGGTAACGGCTCACCAAGGCGACGATGCGTAGCCGACCTGAGAGGGTGACCGGCCACA
            250        260        270        280        290        300

310        320        330        340        350        360
BR   CTGGGACTGAGACACGGCCCAGACTCCTACGGGAGGCAGCAGTAGGGAATCTTCCGCAAT
     ::::::::::::::::::::::::::::::::::::::::::::::::::::::::::::
Bsp  CTGGGACTGAGACACGGCCCAGACTCCTACGGGAGGCAGCAGTAGGGAATCTTCCGCAAT
            310        320        330        340        350        360

370        380        390        400        410        420
BR   GGACGAAAGTCTGACGGAGCAACGCCGCGTGAGCGAAGAAGGTCTTCGGATCGTAAAGCT
     ::::::::::::::::::::::::::::::::::::::::::::::::::::::::::::
Bsp  GGACGAAAGTCTGACGGAGCAACGCCGCGTGAGCGAAGAAGGTCTTCGGATCGTAAAGCT
            370        380        390        400        410        420

430        440        450        460        470        480
BR   CTGTTGTCAGGGAAGAACAAGTACCGTTCGAACAGGGCGGTACCTTGACGGTACCTGACG
     ::::::::::::::::::::::::::::::::::::::::::::::::::::::::::::
Bsp  CTGTTGTCAGGGAAGAACAAGTACCGTTCGAACAGGGCGGTACCTTGACGGTACCTGACG
            430        440        450        460        470        480

490        500
BR   AGGAAGCCACGGCTAACTAC
     ::::::::::::::::::::
Bsp  AGGAAGCCACGGCTAACTAC
            490        500
```

FIG. 7

Comparison of 16S rDNA sequences: BR vs. BP

BR: BR449 16S rDNA - 500 nt
BP: B. pallidus 16S rDNA - 500 nt scoring matrix: , gap penalties: -12/-2

99.6% identity;          Global alignment score: 1986

```
               10        20        30        40        50        60
BR     CTCAGGACGAACGCTGGCGGCGTGCCTAATACATGCAAGTCGAGCGGACCGAAGGGAGCT
       ::::::::::::::::::::::::::::::::::::::::::::::::::::::::::::
BP     CTCAGGACGAACGCTGGCGGCGTGCCTAATACATGCAAGTCGAGCGGACCGAAGGGAGCT
               10        20        30        40        50        60

70        80        90       100       110       120
BR     TGCTCCTTTAGGTTAGCGGCGGACGGGTGAGTAACACGTGGGCAACCTGCCCTGCAGACT
       ::::::::::::::  ::::::::::::::::::::::::::::::::::::::::::::
BP     TGCTCCTTTAGGTTAACGGCGGACGGGTGAGTAACACGTGGGCAACCTGCCCTGCAGACT
               70        80        90       100       110       120

130       140       150       160       170       180
BR     GGGATAACTTCGGGAAACCGGAGCTAATACCGGATAACACCGAAAACCGCATGGTTTTCG
       ::::::::::::::::::::::::::::::::::::::::::::::::::::::::::::
BP     GGGATAACTTCGGGAAACCGGAGCTAATACCGGATAACACCGAAAACCGCATGGTTTTCG
              130       140       150       160       170       180

190       200       210       220       230       240
BR     GTTGAAAGGCGGCTTTTAGCTGTCACTGCAGGATGGGCCCGCGGCGCATTAGCTAGTTGG
       ::::::::::::::::::::::::::::::::::::::::::::::::::::::::::::
BP     GTTGAAAGGCGGCTTTTAGCTGTCACTGCAGGATGGGCCCGCGGCGCATTAGCTAGTTGG
              190       200       210       220       230       240

250       260       270       280       290       300
BR     TGAGGTAACGGCTCACCAAGGCGACGATGCGTAGCCGACCTGAGAGGGTGACCGGCCACA
       ::::::::::::::::::::::::::::::::::::::::::::::::::::::::::::
BP     TGAGGTAACGGCTCACCAAGGCGACGATGCGTAGCCGACCTGAGAGGGTGACCGGCCACA
              250       260       270       280       290       300

310       320       330       340       350       360
BR     CTGGGACTGAGACACGGCCCAGACTCCTACGGGAGGCAGCAGTAGGGAATCTTCCGCAAT
       ::::::::::::::::::::::::::::::::::::::::::::::::::::::::::::
BP     CTGGGACTGAGACACGGCCCAGACTCCTACGGGAGGCAGCAGTAGGGAATCTTCCGCAAT
              310       320       330       340       350       360

370       380       390       400       410       420
BR     GGACGAAAGTCTGACGGAGCAACGCCGCGTGAGCGAAGAAGGTCTTCGGATCGTAAAGCT
       ::::::::::::::::::::::::::::::::::::::::::::::::::::::::::::
BP     GGACGAAAGTCTGACGGAGCAACGCCGCGTGAGCGAAGAAGGTCTTCGGATCGTAAAGCT
              370       380       390       400       410       420

430       440       450       460       470       480
BR     CTGTTGTCAGGGAAGAACAAGTACCGTTCGAACAGGGCGGTACCTTGACGGTACCTGACG
       :::::::::::::::::::::::: :::::::::::::::::::::::::::::::::::
BP     CTGTTGTCAGGGAAGAACAAGTGCCGTTCGAACAGGGCGGTACCTTGACGGTACCTGACG
              430       440       450       460       470       480

490       500
BR     AGGAAGCCACGGCTAACTAC
       ::::::::::::::::::::
BP     AGGAAGCCACGGCTAACTAC
              490       500
```

FIG. 8

Comparison of 16S rDNA sequences: BR vs. BS

BR: BR449 16S rDNA - 500 nt
BS: B.smithii 16S rDNA - 501 nt scoring matrix: , gap penalties: -12/-2

91.7% identity;   Global alignment score: 1659

```
              10        20        30        40        50
BR     CTCAGGACGAACGCTGGCGGCGTGCCTAATACATGCAAGTCGAGCGGACCGA-AGGGAGC
       ::::::::::::::::::::::::::::::::::::::::::::::::::   :  :::
BS     CTCAGGACGAACGCTGGCGGCGTGCCTAATACATGCAAGTCGAGCGGACTTTCAAGAAGC
              10        20        30        40        50        60

60        70        80        90       100       110
BR      TTGCTCCTTTAG-GTTAGCGGCGGACGGGTGAGTAACACGTGGGCAACCTGCCCTGCA-G
        :::::  ::  : ::::::::::::::::::::::::::::::::::::::::: ::::  :
BS      TTGCTTTTTGAAAGTTAGCGGCGGACGGGTGAGTAACACGTGGGCAACCTGCC-TGCAAG
           70        80        90       100       110

120       130       140       150       160       170
BR      ACTGGGATAACTTCGGGAAACCGGAGCTAATACCGGATAACACCGAAAACCGCATGGTTT
        ::  :::::::::: :::::::::::  ::::::::::::::  : :        ::::::
BS      ACGGGGATAACTCCGGGAAACCGGGGCTAATACCGGATAATATCTTCCTTCGCATGAAGG
          120       130       140       150       160       170

180       190       200       210       220       230
BR      TCGGTTGAAAGGCGGCTTTTAGCTGTCACT-GCAGGATGGGCCCGCGGCGCATTAGCTAG
        ::::::::::::::::  ::::  :  :: : ::::::::::::::::::::::::::::::
BS      AAGGTTGAAAGGCGGCGCA-AGCTGCCGCTTGCAG-ATGGGCCCGCGGCGCATTAGCTAG
          180       190       200       210       220       230

240       250       260       270       280       290
BR      TTGGTGAGGTAACGGCTCACCAAGGCGACGATGCGTAGCCGACCTGAGAGGGTGACCGGC
        :::::::::::::::::::::::::::::::::::::::::::::::::::::::::  ::::
BS      TTGGTGAGGTAACGGCTCACCAAGGCGACGATGCGTAGCCGACCTGAGAGGGTGATCGGC
          240       250       260       270       280       290

300       310       320       330       340       350
BR      CACACTGGGACTGAGACACGGCCCAGACTCCTACGGGAGGCAGCAGTAGGGAATCTTCCG
        ::::::::::::::::::::::::::::::::::::::::::::::::::::::::::::::
BS      CACACTGGGACTGAGACACGGCCCAGACTCCTACGGGAGGCAGCAGTAGGGAATCTTCCG
          300       310       320       330       340       350

360       370       380       390       400       410
BR      CAATGGACGAAAGTCTGACGGAGCAACGCCGCGTGAGCGAAGAAGGTCTTCGGATCGTAA
        ::::::::::::::::::::::  ::::::::::::::::::::::::::::::::::::::
BS      CAATGGACGAAAGTCTGACGGCGCAACGCCGCGTGAGCGAAGAAGGTCTTCGGATCGTAA
          360       370       380       390       400       410

420       430       440       450       460       470
BR      AGCTCTGTTGTCAGGGAAGAACAAGTACCGTTCGAACAGGGCGGTACCTTGACGGTACCT
        ::::::::::::::::::::::::::::::::::::::::::::::::::::::::::::
BS      AGCTCTGTTGTCAGGGAAGAACAAGTACCGTTCGAACAGGGCGGTACCTTGACGGTACCT
          420       430       440       450       460       470

480       490       500
BR      GACGAGGAAGCCACGGCTAACTAC
        :::  ::  :::::::::::::::::
BS      GACCAGAAAGCCACGGCTAACTAC
          480       490       500
```

FIG. 9

```
TTTAACTAGGTGTTATAGGGAGAAAAAATTTATATAGGTTTACAAAAAAG
GGCATTCCTATTTATCTTTTCTACATCAATTTGAAAGGGATTATTGTGCT
TTAAATAGTGCGAATTTTCTTGAAATATTTTCGTTCTCACGTTCTATATT
TTTTACCTTTTAAAAAATCATTAATAAATGCAATCATCCTATCTTTACTT
CTTAGTCTTCAAACAGCGTGAACCACTAATAGAGCTTCTTTTAACTTTTT
CATATGATGATGTGATGCCGCCAGACATACTTAAAAACTATGCATTGATT
CATTTAGACATTCTTTAAGAGAAAATAGTTAGATTTAAAGGAGGTGATGC
CTGGGGAAATCGAACAGCAGGTCTATATATTATTATATTTAATTCACTTC
CAACATTTTATAACAAAAGGAGGAAAAAGGCATGAGACACGGGGATATTT      - amidase gene
CAAGCAGCCACGACACAGTAGGAATAGCGGTGGTCAATTACAAAATGCCG        (348 aa)
CGTTTGCACACGAAAGCAGAAGTTATTGAAAATGCAAAAAGATCGCTGA
CATGGTCGTAGGGATGAAGCAAGGTCTTCCAGGTATGGATCTCGTCGTTT
TCCCGGAGTACAGCACAATGGGAATTATGTACGATCAGGATGAAATGTTT
GCCACTGCAGCTTCCATACCAGGAGAGGAAACAGCTATCTTTGCTGAAGC
GTGCAAAAAGGCTGATACATGGGGGGTATTCTCACTAACCGGGGAAAAAC
ATGAAGATCATCCGAATAAGGCACCATACAACACCCTAGTTCTCATTAAT
AACAAAGGAGAGATTGTGCAAAAGTACCGCAAGATTATTCCTTGGTGTCC
GATCGAAGGATGGTATCCGGGAGATACCACTTATGTCACGGAAGGACCGA
AGGGGTTGAAAATCAGTCTCATCGTTTGTGATGACGGAAATTATCCTGAA
ATCTGGCGCGATTGTGCGATGAAAGGCGCAGAATTGATCGTCCGTTGCCA
AGGCTACATGTATCCGGCAAAAGAGCAGCAAATCATGATGGCGAAAGCTA
TGGCTTGGGCGAACAATACCTATGTAGCCGTTGCCAACGCAACAGGATTT
GACGGAGTTTATTCATATTTTGGCCACTCTGCCATCATCGGTTTTGACGG
ACGCACACTAGGTGAGTGCGGAACGGAGGAGAATGGTATACAGTACGCAG
AAGTGTCCATCTCTCAGATTCGTGATTTTAGAAAGAACGCCCAGTCCCAA
AATCATTTGTTCAAGCTGCTTCACCGAGGCTATACTGGCTTGATCAACTC
CGGAGAAGGCGACCGAGGCGTAGCAGAATGCCCATTTGATTTTTATCGCA
CTTGGGTACTCGATGCAGAAAAGGCAAGAGAAAATGTAGAGAAGATCACT
AGAAGTACGGTTGGGACAGCAGAATGTCCGATTCAAGGAATCCCAAATGA
AGGAAAAACAAAAGAAATTGGTGTGTAATTCTGGAATACCAATTGTTTAA
TGCACAATAACTGCATTTTCGTCATTTTCCTTAAGTGTTAAATGAGATGA
CTAACATATGTCATCGGTAAAAATAAATTCTTAATCAAAGATGGGAGGTA
AACAAATGAACGGTATTCATGATGTTGGAGGCATGGATGGATTTGGAAAA      - beta subunit gene
GTGATGTATGTAAAAGAAGAAGAGGACATTTATTTTACACATGATTGGGA
AAGACTTGCGTTCGGACTTGTAGCTGGTTGTATGGCACAAGGATTGGGGA
TGAAGGCTTTTGATGAATTCAGGATCGGCATTGAGCTTATGCGTCCAGTG
GATTATTTGACGTCGTCGTATTATGGCCATTGGATTGCAACTGTTGCATA
CAACTTAGTAGATACGGGAGTATTAGACGAAAAGAACTAGATGAACGAA
CGGAGGTTTTCTTGAAGAAACCTGATACTAACCAAAATACCACGAAGAGAGGAT
CCGGCATTAGTGAAGCTTGTAGAAAAGGCACTGTATGAAGGCTTATCTCC
GATCCGTGAAATTTCAGCTTCTCCTCGGTTTAAGGTAGGAGAGAGAATCA
AGACGAAAAACATTCATCCAACTGGTCATACGAGATTCCCTCGATATGCC
CGTGACAAATATGGTGTCATTGATGAGATATATGGAGCTCATGTTTTCCC
TGATGATGCTGCTCATAGAAAGGAGAAAACCCGCAATATCTTTACCGGG
TACGTTTTGAGGCTGAAGAATTATGGGGATATAAACAGAAAGATTCCGTT
TATATAGATCTATGGGAAAGTTATATGGAGCCTGTTTCACATTAATCATT      - alpha subunit gene
TTTTGAAGGAGGAATACAATATGACGATTGATCAAAAAAATACTAATATA
GATCCAAGATTTCCACATCATCATCCGCGTCCACAATCATTTTGGGAGGC
ACGTGCAAAAGCTCTTGAATCCTTGTTGATTGAGAAAGGGCATCTTTCCT
CAGATGCTATTGAAAGGGTAATAAAACATTATGAGCATGAGCTGGGACCA
ATGAACGGAGCAAAGGTCGTAGCGAAGGCTTGGACTGATCCTGCTTTTAA
ACAAAGATTGCTAGAAGATCCAGAGACTGTATTAAGGGAGCTAGGATACT
ATGGTTTACAGGGTGAGCATATCAGGGTAGTAGAAAATACGGATACGGTA
CACAATGTTGTAGTCTGCACTTTATGTTCATGTTACCCTTGGCCATTGCT
TGGTTTACCGCCTTCATGGTACAAAGAACCTGCTTATAGAGCTCGTGTCG
TAAAAGAGCCGAGACAAGTGTTGAAAGAATTCGGATTAGATCTTCCAGAT
TCAGTAGAAATCCGGGTATGGGACAGCAGTTCAGAAATTCGCTTTATGGT
ATTGCCGCAAAGACCTGAAGGTACGGAAGGAATGACGGAGGAGGAGCTTG
CAAAACTTGTTACTCGAGACTCCATGATTGGTGTCGCTAAAATAGAGCCG
CTAAAGTTACGGTAGGTTAGGAGGAAAATAATGAAAAGTTGTGAGAATCA      - orf1
ACCTAATGAATCATTGCTTGCGAATATGTCTGAAGAAGTCGCACCTCCTA
GAAAAAACGGAGAGTTAGAATTCCAAGAGCCTTGGGAAAGACGCTCTTTT
GGCATGACTCTTGCTTTGTACGAAGAAAAGCTGTATAGCTCTTGGGAGGA
TTTTCGATCCCGCTTGATTGAGGAGATCAAGGGGTGGGAGACCGCGAAAC
AGAAGGAGAATTCTGACTGGAACTACTATGAGCATTGGCTGGCCGCCTTG
GAACGACTAGTAGTGGAAACAGGAATGTTAAATTAAGCGTGATGTCGAC
                                             SalI
```

FIG. 10

```
Met Thr Ile Asp Gln Lys Asn Thr Asn Ile Asp Pro Arg Phe Pro His
 1               5                   10                  15

His His Pro Arg Pro Gln Ser Phe Trp Glu Ala Arg Ala Lys Ala Leu
             20                  25                  30

Glu Ser Leu Leu Ile Glu Lys Gly His Leu Ser Ser Asp Ala Ile Glu
         35                  40                  45

Arg Val Ile Lys His Tyr Glu His Glu Leu Gly Pro Met Asn Gly Ala
         50                  55                  60

Lys Val Val Ala Lys Ala Trp Thr Asp Pro Ala Phe Lys Gln Arg Leu
 65                  70                  75                  80

Leu Glu Asp Pro Glu Thr Val Leu Arg Glu Leu Gly Tyr Tyr Gly Leu
                 85                  90                  95

Gln Gly Glu His Ile Arg Val Val Glu Asn Thr Asp Thr Val His Asn
             100                 105                 110

Val Val Val Cys Thr Leu Cys Ser Cys Tyr Pro Trp Pro Leu Leu Gly
             115                 120                 125

Leu Pro Pro Ser Trp Tyr Lys Glu Pro Ala Tyr Arg Ala Arg Val Val
     130                 135                 140

Lys Glu Pro Arg Gln Val Leu Lys Glu Phe Gly Leu Asp Leu Pro Asp
 145                 150                 155                 160

Ser Val Glu Ile Arg Val Trp Asp Ser Ser Glu Ile Arg Phe Met
                 165                 170                 175

Val Leu Pro Gln Arg Pro Glu Gly Thr Glu Gly Met Thr Glu Glu Glu
             180                 185                 190

Leu Ala Lys Leu Val Thr Arg Asp Ser Met Ile Gly Val Ala Lys Ile
         195                 200                 205

Glu Pro Leu Lys Leu Arg
 210
```

FIG. 11

Met Asn Gly Ile His Asp Val Gly Gly Met Asp Gly Phe Gly Lys Val
1               5                   10                  15

Met Tyr Val Lys Glu Glu Glu Asp Ile Tyr Phe Thr His Asp Trp Glu
            20                  25                  30

Arg Leu Ala Phe Gly Leu Val Ala Gly Cys Met Ala Gln Gly Leu Gly
            35                  40                  45

Met Lys Ala Phe Asp Glu Phe Arg Ile Gly Ile Glu Leu Met Arg Pro
            50                  55                  60

Val Asp Tyr Leu Thr Ser Ser Tyr Tyr Gly His Trp Ile Ala Thr Val
65              70                  75                      80

Ala Tyr Asn Leu Val Asp Thr Gly Val Leu Asp Glu Lys Glu Leu Asp
                85                  90                  95

Glu Arg Thr Glu Val Phe Leu Lys Lys Pro Asp Thr Lys Ile Pro Arg
                100                 105                 110

Arg Glu Asp Pro Ala Leu Val Lys Leu Val Glu Lys Ala Leu Tyr Glu
            115                 120                 125

Gly Leu Ser Pro Ile Arg Glu Ile Ser Ala Ser Pro Arg Phe Lys Val
            130                 135                 140

Gly Glu Arg Ile Lys Thr Lys Asn Ile His Pro Thr Gly His Thr Arg
145                 150                 155                 160

Phe Pro Arg Tyr Ala Arg Asp Lys Tyr Gly Val Ile Asp Glu Ile Tyr
                165                 170                 175

Gly Ala His Val Phe Pro Asp Asp Ala Ala His Arg Lys Gly Glu Asn
                180                 185                 190

Pro Gln Tyr Leu Tyr Arg Val Arg Phe Glu Ala Glu Leu Trp Gly
            195                 200                 205

Tyr Lys Gln Lys Asp Ser Val Tyr Ile Asp Leu Trp Glu Ser Tyr Met
            210                 215                 220

Glu Pro Val Ser His
225

FIG. 12

```
Met Arg His Gly Asp Ile Ser Ser Ser His Asp Thr Val Gly Ile Ala
 1               5                   10                  15
Val Val Asn Tyr Lys Met Pro Arg Leu His Thr Lys Ala Glu Val Ile
             20                  25                  30
Glu Asn Ala Lys Lys Ile Ala Asp Met Val Val Gly Met Lys Gln Gly
         35                  40                  45
Leu Pro Gly Met Asp Leu Val Val Phe Pro Glu Tyr Ser Thr Met Gly
     50                  55                  60
Ile Met Tyr Asp Gln Asp Glu Met Phe Ala Thr Ala Ala Ser Ile Pro
 65              70                  75                  80
Gly Glu Glu Thr Ala Ile Phe Ala Glu Ala Cys Lys Lys Ala Asp Thr
                 85                  90                  95
Trp Gly Val Phe Ser Leu Thr Gly Glu Lys His Glu Asp His Pro Asn
             100                 105                 110
Lys Ala Pro Tyr Asn Thr Leu Val Leu Ile Asn Asn Lys Gly Glu Ile
         115                 120                 125
Val Gln Lys Tyr Arg Lys Ile Ile Pro Trp Cys Pro Ile Glu Gly Trp
     130                 135                 140
Tyr Pro Gly Asp Thr Thr Tyr Val Thr Glu Gly Pro Lys Gly Leu Lys
145                 150                 155                 160
Ile Ser Leu Ile Val Cys Asp Asp Gly Asn Tyr Pro Glu Ile Trp Arg
             165                 170                 175
Asp Cys Ala Met Lys Gly Ala Glu Leu Ile Val Arg Cys Gln Gly Tyr
         180                 185                 190
Met Tyr Pro Ala Lys Glu Gln Gln Ile Met Met Ala Lys Ala Met Ala
     195                 200                 205
```

FIG. 13A

```
Trp Ala Asn Asn Thr Tyr Val Ala Val Ala Asn Ala Thr Gly Phe Asp
        210             215             220

Gly Val Tyr Ser Tyr Phe Gly His Ser Ala Ile Ile Gly Phe Asp Gly
225             230             235                     240

Arg Thr Leu Gly Glu Cys Gly Thr Glu Glu Asn Gly Ile Gln Tyr Ala
            245             250                     255

Glu Val Ser Ile Ser Gln Ile Arg Asp Phe Arg Lys Asn Ala Gln Ser
            260             265             270

Gln Asn His Leu Phe Lys Leu Leu His Arg Gly Tyr Thr Gly Leu Ile
        275             280             285

Asn Ser Gly Glu Gly Asp Arg Gly Val Ala Glu Cys Pro Phe Asp Phe
        290             295             300

Tyr Arg Thr Trp Val Leu Asp Ala Glu Lys Ala Arg Glu Asn Val Glu
305             310             315                     320

Lys Ile Thr Arg Ser Thr Val Gly Thr Ala Glu Cys Pro Ile Gln Gly
                325             330                     335

Ile Pro Asn Glu Gly Lys Thr Lys Glu Ile Gly Val
            340             345
```

FIG. 13B

```
Met Lys Ser Cys Glu Asn Gln Pro Asn Glu Ser Leu Leu Ala Asn Met
 1               5                   10                  15

Ser Glu Glu Val Ala Pro Pro Arg Lys Asn Gly Glu Leu Glu Phe Gln
                20                  25                  30

Glu Pro Trp Glu Arg Arg Ser Phe Gly Met Thr Leu Ala Leu Tyr Glu
            35                  40                  45

Glu Lys Leu Tyr Ser Ser Trp Glu Asp Phe Arg Ser Arg Leu Ile Glu
        50                  55                  60

Glu Ile Lys Gly Trp Glu Thr Ala Lys Gln Lys Glu Asn Ser Asp Trp
 65              70                  75                      80

Asn Tyr Tyr Glu His Trp Leu Ala Ala Leu Glu Arg Leu Val Val Glu
                85                  90                  95

Thr Gly Met Leu Asn
            100
```

FIG. 14

Comparison of alpha subunit genes: BR vs. BS
BR-A: BR449 (642 nt); BS-A: B. smithii (660 nt)
81.4% identity;

```
              10        20        30        40
BR-A    ATGACGATTGATCAAAAAA------------ATACTAATATAGATCCAAGATTTCCACAT
        ::: : ::::: ::::::              ::  : :  ::::: ::::::::::::
BS-A    ATGGCAATTGAACAAAAATTGATGGATGATCATCATGAAGTGGATCCGCGATTTCCACAT
              10        20        30        40        50        60

50        60        70        80        90       100
BR-A    CATCATCCGCGTCCACAATCATTTTGGGAGGCACGTGCAAAAGCTCTTGAATCCTTGTTG
        :::::::: ::  ::::: :::::::::: :::::  : ::::: :::::::::  ::::
BS-A    CATCATCCCCGGCCGCAATCGTTTTGGGAAGCACGGGCTAAAGCGCTTGAATCTCTGTTA
              70        80        90       100       110       120

110       120       130       140       150       160
BR-A    ATTGAGAAAGGGCATCTTTCCTCGATGCTATTGAAAGGGTAATAAAACATTATGAGCAT
        ::::::::::   :  ::::::::::: ::  :::::  :::::  :::::::: :::
BS-A    ATTGAGAAAAGACTTCTTTCCTCTGACGCCATTGAGAGGGTTATAAAACACTATGAACAT
             130       140       150       160       170       180

170       180       190       200       210       220
BR-A    GAGCTGGGACCAATGAACGGAGCAAAGGTCGTAGCGAAGGCTTGGACTGATCCTGCTTTT
        ::::: :: :: :::::::::::: :::::::: ::::: ::: ::::::::::  :::
BS-A    GAGCTTGGGCCGATGAACGGAGCTAAAGTCGTTGCGAAGGCCTGGACCGATCCTGAATTT
             190       200       210       220       230       240

230       240       250       260       270       280
BR-A    AAACAAAGATTGCTAGAAGATCCAGAGACTGTATTAAGGGAGCTAGGATACTATGGTTTA
        :::::::::::::: :: :::::::: :::::::  ::::  :: :::: :::: :  :
BS-A    AAACAAAGATTGCTGGAAGATCCAGAAACTGTGTTGCGGGAACTTGGATATTTTGGTCTG
             250       260       270       280       290       300

290       300       310       320       330       340
BR-A    CAGGGTGAGCATATCAGGGTAGTAGAAAATACGGATACGGTACACAATGTTGTAGTCTGC
        :: :: ,::::::::::::::: ::: ::::::::::::::::::::::::: :: :::
BS-A    CAAGGAGAGCATATCAGGGTAGTGGAAAATACGGATACGGTACACAATGTAGTGGTTTGC
             310       320       330       340       350       360

350       360       370       380       390       400
BR-A    ACTTTATGTTCATGTTACCCTTGGCCATTGCTTGGTTTACCGCCTTCATGGTACAAAGAA
        ::: :::::::::::::: ::::::: :::::::::::::::::::::::::: :::::
BS-A    ACTCTATGTTCATGTTATCCTTGGCCGCTGCTTGGTTTACCGCCTTCATGGTATAAAGAA
             370       380       390       400       410       420

410       420       430       440       450       460
BR-A    CCTGCTTATAGAGCTCGTGTCGTAAAAGAGCCGAGACAAGTGTTGAAAGAATTCGGATTA
        ::  ::  :: :  : :: :: :::::::::::::  :::  :: :::::::::::::::
BS-A    CCGGCCTACCGTTCTCGGGTTGTTAAAGAGCCGAGAAAAGTACTGCAAGAATTCGGATTA
             430       440       450       460       470       480

470       480       490       500       510       520
BR-A    GATCTTCCAGATTCAGTAGAAATCCGGGTATGGGACAGCAGTTCAGAAATTCGCTTTATG
        ::  :  :: ::::::::::::::  :::: :::::: ::::::::: :::  ::::::
BS-A    GACTTGCCGGATTCAGTAGAAATTCGGGTTTGGGACAGTAGTTCAGAAGTTCGTTTTATG
             490       500       510       520       530       540

530       540       550       560       570       580
BR-A    GTATTGCCGCAAAGACCTGAAGGTACGGAAGGAATGACGGAGGAGGAGCTTGCAAAACTT
        ::::::::::::::::::::  ::  ::::::::::::::::::::::::  ::  :  :
BS-A    GTATTGCCGCAAAGACCTGAGGGCACAGAAGGAATGACGGAGGAGGAGCTGGCGCAAATC
             550       560       570       580       590       600

590       600       610       620       630       640
BR-A    GTTACTCGAGACTCCATGATTGGTGTCGCTAAAATAGAGCCGC-TAAAGTTACGG-----
        :::::: :: ::::::::::::: :::::  :: :::::  :::: ::::::::
BS-A    GTTACTCGTGACTCCATGATTGGCGTCGCCAAAGTTCAGCCGCCTAAAGTGATCCAAGAA
             610       620       630       640       650       660
```

FIG. 15

Comparison of alpha subunit proteins: BR vs. BS
BR-B: BR449 (214 aa); BS-B: B. smithii (220 aa)
87.7% identity;

```
              10         20         30         40         50
BR-B    MTIDQK----NTNIDPRFPHHHPRPQSFWEARAKALESLLIEKGHLSSDAIERVIKHYEH
        :.:.::    . ..::::::::::::::::::::::::::    ::::::::::::::
BS-B    MAIEQKLMDDHHEVDPRFPHHHPRPQSFWEARAKALESLLIEKRLLSSDAIERVIKHYEH
              10         20         30         40         50         60

60         70         80         90        100       110
BR-B    ELGPMNGAKVVAKAWTDPAFKQRLLEDPETVLRELGYYGLQGEHIRVVENTDTVHNVVVC
        ::::::::::::::::::: ::::::::::::::::::: ::::::::::::::::::::
BS-B    ELGPMNGAKVVAKAWTDPEFKQRLLEDPETVLRELGYFGLQGEHIRVVENTDTVHNVVVC
              70         80         90        100       110       120

120        130        140        150        160       170
BR-B    TLCSCYPWPLLGLPPSWYKEPAYRARVVKEPRQVLKEFGLDLPDSVEIRVWDSSSEIRFM
        :::::::::::::::::::::::::::.:::.:::::::::::::::::::::::.:::
BS-B    TLCSCYPWPLLGLPPSWYKEPAYRSRVVKEPRKVLQEFGLDLPDSVEIRVWDSSSEVRFM
             130        140        150        160        170       180

180        190        200        210
BR-B    VLPQRPEGTEGMTEEELAKLVTRDSMIGVAKIEPLKL--R
        ::::::::::::::::::::..::::::::::::..:  .
BS-B    VLPQRPEGTEGMTEEELAQIVTRDSMIGVAKVQPPKVIQE
             190        200        210        220
```

FIG. 16

Comparison of beta subunit genes: BR vs. BS
BR-B: BR449 (687 nt); BS-B: B. smithii (687 nt)
82.5% identity;

```
              10        20        30        40        50        60
BR-B   ATGAACGGTATTCATGATGTTGGAGGCATGGATGGATTTGGAAAAGTGATGTATGTAAAA
       ::::: :: ::::::::::::: :::::::::::::::::: ::: : ::::::::: :::
BS-B   ATGAATGGGATTCATGATGTTGGCGGCATGGATGGATTTGGGAAAATTATGTATGTGAAA
              10        20        30        40        50        60

70        80        90       100       110       120
BR-B   GAAGAAGAGGACATTTATTTTACACATGATTGGGAAAGACTTGCGTTCGGACTTGTAGCT
       ::::: :: :: : :::::: : :::::::::::::::: ::: : ::::: ::::: ::
BS-B   GAAGAGGAAGATACTTATTTCAAACATGATTGGGAAAGGCTTACTTTCGGTCTTGTTGCC
              70        80        90       100       110       120

130       140       150       160       170       180
BR-B   GGTTGTATGGCACAAGGATTGGGGATGAAGGCTTTTGATGAATTCAGGATCGGCATTGAG
       :: :: ::::: ::::::::::::: ::::::::::::::::::: ::::: ::::::::
BS-B   GGCTGCATGGCTCAAGGATTGGGAATGAAGGCTTTTGATGAATTTAGGATTGGCATTGAA
              130       140       150       160       170       180

190       200       210       220       230       240
BR-B   CTTATGCGTCCAGTGGATTATTTGACGTCGTCGTATTATGGCCATTGGATTGCAACTGTT
       ::::::::::: ::::: :: :: ::::::: ::: ::::: ::::::::::::: :: 
BS-B   AAAATGCGTCCAGTTGATTATCTGACATCATCCTATTATGGTCATTGGATTGCAACCGTC
              190       200       210       220       230       240

250       260       270       280       290       300
BR-B   GCATACAACTTAGTAGATACGGGAGTATTAGACGAAAAAAGAACTAGATGAACGAACGGAG
       ::::::::::: :: :: ::::::::::: :: ::::::::::: :: :: ::::: : 
BS-B   GCATACAACTTGTTGGAAACGGGAGTACTGGATGAAAAAGAATTGGAAGATCGAACACAA
              250       260       270       280       290       300

310       320       330       340       350       360
BR-B   GTTTTCTTGAAGAAACCTGATACCAAAATACCACGAAGAGAGGATCCGGCATTAGTGAAG
       : :::: :: : ::::: :: ::::::::: ::: : ::: :::::  :::::: :::
BS-B   GCTTTCATGGAAAAACCCGACACCAAAATACAACGTTGGGAGAATCCGAAATTAGTTAAG
              310       320       330       340       350       360

370       380       390       400       410       420
BR-B   CTTGTAGAAAAGGCACTGTATGAAGGCTTATCTCCGATCCGTGAAATTTCAGCTTCTCCT
       ::::::::::: :: ::: ::::: :::::::::: :::::::::: :  : : :::
BS-B   GTTGTAGAAAAAGCCCTGCTTGAAGGTTTATCTCCTGTCCGTGAAGTTTCCTCATTTCCA
              370       380       390       400       410       420

430       440       450       460       470       480
BR-B   CGGTTTAAGGTAGGAGAGAGAATCAAGACGAAAAACATTCATCCAACTGGTCATACGAGA
       ::::::  ::: :::::::: :::::: :::: :  : :::::::::: :: :: :: :::
BS-B   CGGTTTGAGGTGGGAGAAAAGAATAAAGACAAGGAACATTCACCCAACAGGCCACACTAGA
              430       440       450       460       470       480

490       500       510       520       530       540
BR-B   TTCCCTCGATATGCCCGTGACAAATATGGTGTCATTGATGAGATATATGGAGCTCATGTT
       :: :: ::::: :  :: :: :: ::::: ::: :::::: :: ::::::: :::::::
BS-B   TTTCCACGATACGTGCGCGATAAGTATGGAGTCATTGAAGAGGTATATGGGGCTCATGTT
              490       500       510       520       530       540

550       560       570       580       590       600
BR-B   TTCCCTGATGATGCTGCTCATAGAAAAGGAGAAAAACCCGCAATATCTTTACCGGGTACGT
       ::::::::::: :::::::::::::::::::::::::::::::::::::: :: :: :::::
BS-B   TTCCCTGATGACGCTGCTCACAGAAAAGGAGAAAAACCCGCAATATCTCTATCGTGTACGT
              550       560       570       580       590       600

610       620       630       640       650       660
BR-B   TTTGAGGCTGAAGAATTATGGGGATATAAACAGAAAGATTCCGTTTATATAGATCTATGG
       ::::: :::::::::::::::::::       ::::::::: ::::: :::::::::: :::
BS-B   TTTGATGCCGAAGAATTATGGGGAGTAAAACAGAATGATTCAGTTTATATCGATCTTTGG
              610       620       630       640       650       660

670       680
BR-B   GAAAGTTATATGGAGCCTGTTTCACAT
       ::: ::::: :::: :::::::::::
BS-B   GAAGGTTATTTGGAACCTGTTTCACAT
              670       680
```

FIG. 17

Comparison of beta subunit proteins: BR vs. BS
BR-B: BR449 (229 aa); BS-B: B. smithii (229 aa)
85.6% identity;

```
              10        20        30        40        50        60
BR-B   MNGIHDVGGMDGFGKVMYVKEEEDIYFTHDWERLAFGLVAGCMAQGLGMKAFDEFRIGIE
       ::::::::::::::: :::::::: ::  :::::: :::::::::::::::::::::::
BS-B   MNGIHDVGGMDGFGKIMYVKEEEDTYFKHDWERLTFGLVAGCMAQGLGMKAFDEFRIGIE
              10        20        30        40        50        60

70        80        90       100       110       120
BR-B   LMRPVDYLTSSYYGHWIATVAYNLVDTGVLDEKELDERTEVFLKKPDTKIPRREDPALVK
        ::::::::::::::::::::::::  ::::::::::  ::  :  ::::: : :: :::
BS-B   KMRPVDYLTSSYYGHWIATVAYNLLETGVLDEKELEDRTQAFMEKPDTKIQRWENPKLVK
              70        80        90       100       110       120

130       140       150       160       170       180
BR-B   LVEKALYEGLSPIREISASPRFKVGERIKTKNIHPTGHTRFPRYARDKYGVIDEIYGAHV
        :::::  ::::: ::  : ::::: ::::::: ::::::::::::: :::::: : :::
BS-B   VVEKALLEGLSPVREVSSFPRFEVGERIKTRNIHPTGHTRFPRYVRDKYGVIEEVYGAHV
             130       140       150       160       170       180

190       200       210       220
BR-B   FPDDAAHRKGENPQYLYRVRFEAEELWGYKQKDSVYIDLWESYMEPVSH
       ::::::::::::::::::::::: ::::::: :::::::::::  ::::
BS-B   FPDDAAHRKGENPQYLYRVRFDAEELWGVKQNDSVYIDLWEGYLEPVSH
             190       200       210       220
```

FIG. 18

Homology search of ORF1 (101 aa)

gnl|PID|d1012733 (D83695) nitrile hydratase b-subunit homolog [Rhodococcus
          rhodochrous]
          Length = 148

Score = 77.6 bits (188), Expect = 2e-14
 Identities = 40/107 (37%), Positives = 61/107 (56%), Gaps = 9/107 (8%)

Query: 1    MKSCENQPNESLLANMSEEVAP-------PRKNGELEFQEPWERRSFGMTLALYEEKLYS 53
            M     QP+  L AN+ + V         PR++GE+ F + WE R+F +  AL+ +  +
Sbjct: 1    MPRLNEQPHPGLEANLGDLVQNLPFNERIPRRSGEVAFDQAWEIRAFSIATALHGQGRF- 59

Query: 54   SWEDFRSRLIEEIKGWETAKQKENSDWNYYEHWLAALERLVVETGML 100
            W++F+SRLIE IK WE A+        W+YYE W+ ALE L+ + G +
Sbjct: 60   EWDEFQSRLIESIKQWE-AEHATTEQWSYYERWMLALEELLHDKGFV 105

FIG. 19

PstI-SalI DNA fragment (2645 nt) which exhibits Nitrile Hydratase Activity in *E. coli* DH5α

```
PstI
CTGCAGCTTCCATACCAGGAGAGGAAACAGCTATCTTTGCTGAAGCGTGC
AAAAAGGCTGATACATGGGGGGTATTCTCACTAACCGGGGAAAAACATGA
AGATCATCCGAATAAGGCACCATACAACACCCTAGTTCTCATTAATAACA
AAGGAGAGATTGTGCAAAAGTACCGCAAGATTATTCCTTGGTGTCCGATC
GAAGGATGGTATCCGGGAGATACCACTTATGTCACGGAAGGACCGAAGGG
GTTGAAAATCAGTCTCATCGTTTGTGATGACGGAAATTATCCTGAAATCT
GGCGCGATTGTGCGATGAAAGGCGCAGAATTGATCGTCCGTTGCCAAGGC
TACATGTATCCGGCAAAAGAGCAGCAAATCATGATGGCGAAAGCTATGGC
TTGGGCGAACAATACCTATGTAGCCGTTGCCAACGCAACAGGATTTGACG
GAGTTTATTCATATTTTGGCCACTCTGCCATCATCGGTTTGACGGACGC
ACACTAGGTGAGTGCGGAACGGAGGAGAATGGTATACAGTACGCAGAAGT
GTCCATCTCTCAGATTCGTGATTTTAGAAAGAACGCCCAGTCCCAAAATC
ATTTGTTCAAGCTGCTTCACCGAGGCTATACTGGCTTGATCAACTCCGGA
GAAGGCGACCGAGGCGTAGCAGAATGCCCATTTGATTTTTATCGCACTTG
GGTACTCGATGCAGAAAAGGCAAGAGAAAATGTAGAGAAGATCACTAGAA
GTACGGTTGGGACAGCAGAATGTCCGATTCAAGGAATCCCAAATGAAGGA
AAAACAAAAGAAATTGGTGTGTAATTCTGGAATACCAATTGTTTAATGCA
CAATAACTGCATTTTCGTCATTTTCCTTAAGTGTTAAATGAGATGACTAA
CATATGTCATCGGTAAAAATAAATTCTTAATCAAAGATGGGAGGTAAACA
AATGAACGGTATTCATGATGTTGGAGGCATGGATGGATTTGGAAAAGTGA  - beta subunit gene
TGTATGTAAAAGAAGAAGAGGACATTTATTTTACACATGATTGGGAAAGA
CTTGCGTTCGGACTTGTAGCTGGTTGTATGGCACAAGGATTGGGGATGAA
GGCTTTTGATGAATTCAGGATCGGCATTGAGCTTATGCGTCCAGTGGATT
ATTTGACGTCGTCGTATTATGGCCATTGGATTGCAACTGTTGCATACAAC
TTAGTAGATACGGGAGTATTAGACGAAAAAGAACTAGATGAACGAACGGA
GGTTTTCTTGAAGAAACCTGATACCAAAATACCACGAAGAGAGGATCCGG
CATTAGTGAAGCTTGTAGAAAAGGCACTGTATGAAGGCTTATCTCCGATC
CGTGAAATTTCAGCTTCTCCTCGGTTTAAGGTAGGAGAGAGAATCAAGAC
GAAAAACATTCATCCAACTGGTCATACGAGATTCCCTCGATATGCCCGTG
ACAAATATGGTGTCATTGATGAGATATATGGAGCTCATGTTTTCCCTGAT
GATGCTGCTCATAGAAAAGGAGAAAACCCGCAATATCTTTACCGGGTACG
TTTTGAGGCTGAAGAATTATGGGGATATAAACAGAAAGATTCCGTTTATA
TAGATCTATGGGAAAGTTATATGGAGCCTGTTTCACATTAATCATTTTTT
GAAGGAGGAATACAATATGACGATTGATCAAAAAAATACTAATATAGATC  - alpha subunit gene
CAAGATTTCCACATCATCATCCGCGTCCACAATCATTTTGGGAGGCACGT
GCAAAAGCTCTTGAATCCTTGTTGATTGAGAAAGGGCATCTTTCCTCAGA
TGCTATTGAAAGGGTAATAAAACATTATGAGCATGAGCTGGGACCAATGA
ACGGAGCAAAGGTCGTAGCGAAGGCTTGGACTGATCCTGCTTTTAAACAA
AGATTGCTAGAAGATCCAGAGACTGTATTAAGGGAGCTAGGATACTATGG
TTTACAGGGTGAGCATATCAGGGTAGTAGAAAATACGGATACGGTACACA
ATGTTGTAGTCTGCACTTTATGTTCATGTTACCCTTGGCCATTGCTTGGT
TTACCGCCTTCATGGTACAAAGAACCTGCTTATAGAGCTCGTGTCGTAAA
AGAGCCGAGACAAGTGTTGAAAGAATTCGGATTAGATCTTCCAGATTCAG
TAGAAATCCGGGTATGGGACAGCAGTTCAGAAATTCGCTTTATGGTATTG
CCGCAAAGACCTGAAGGTACGGAAGGAATGACGGAGGAGGAGCTTGCAAA
ACTTGTTACTCGAGACTCCATGATTGGTGTCGCTAAAATAGAGCCGCTAA
AGTTACGGTAGGTTAGGAGGAAAATAATGAAAAGTTGTGAGAATCAACCT  - orf1
AATGAATCATTGCTTGCGAATATGTCTGAAGAAGTCGCACCTCCTAGAAA
AAACGGAGAGTTAGAATTCAAGAGCCTTGGGAAAGACGCTCTTTTGGCA
TGACTCTTGCTTTGTACGAAGAAAGCTGTATAGCTCTTGGGAGGATTTT
CGATCCCGCTTGATTGAGGAGATCAAGGGGTGGGAGACCGCGAAACAGAA
GGAGAATTCTGACTGGAACTACTATGAGCATTGGCTGGCCGCCTTGGAAC
GACTAGTAGTGGAAACAGGAATGTTAAATTAAGCGTGATGTCGAC
                                             SalI
```

FIG. 20

SEQUENCE LISTING

```
<160> NUMBER OF SEQ ID NOS:  18

<210> SEQ ID NO 1
<211> LENGTH: 500
<212> TYPE: DNA
<213> ORGANISM: BR449
<220> FEATURE:
<221> NAME/KEY: rRNA
<222> LOCATION: (1)..(500)

<400> SEQUENCE: 1
ctcaggacga acgctggcgg cgtgcctaat acatgcaagt cgagcggacc gaagggagct      60
tgctccttta ggttagcggc ggacgggtga gtaacacgtg ggcaacctgc cctgcagact     120
gggataactt cgggaaaccg gagctaatac cggataacac cgaaaaccgc atggttttcg     180
gttgaaaggc ggctttttagc tgtcactgca ggatgggccc gcggcgcatt agctagttgg     240
tgaggtaacg gctcaccaag gcgacgatgc gtagccgacc tgagagggtg accggccaca     300
ctgggactga gacacggccc agactcctac gggaggcagc agtagggaat cttccgcaat     360
ggacgaaagt ctgacggagc aacgccgcgt gagcgaagaa ggtcttcgga tcgtaaagct     420
ctgttgtcag ggaagaacaa gtaccgttcg aacagggcgg taccttgacg gtacctgacg     480
aggaagccac ggctaactac                                                 500

<210> SEQ ID NO 2
<211> LENGTH: 1517
<212> TYPE: DNA
<213> ORGANISM: Bacillus sp.
<220> FEATURE:
<221> NAME/KEY: rRNA
<222> LOCATION: (1)..(1517)
<308> DATABASE ACCESSION NUMBER: Z26929
```

<309> DATABASE ENTRY DATE: 1998-07-02

<400> SEQUENCE: 2

| | | | | | |
|---|---|---|---|---|---|
| tggctcagga | cgaacgctgg | cggcgtgcct | aatacatgca | agtcgagcgg | accgaaggga | 60 |
| gcttgctcct | ttaggttagc | ggcggacggg | tgagtaacac | gtgggcaacc | tgccctgcag | 120 |
| actgggataa | cttcgggaaa | ccggagctaa | taccggataa | caccgaaaac | cgcatggttt | 180 |
| tcggttgaaa | ggcggctttt | agctgtcact | gcaggatggg | cccgcggcgc | attagctagt | 240 |
| tggtgaggta | acggctcacc | aaggcgacga | tgcgtagccg | acctgagagg | gtgaccggcc | 300 |
| acactgggac | tgagacacgg | cccagactcc | tacgggaggc | agcagtaggg | aatcttccgc | 360 |
| aatggacgaa | agtctgacgg | agcaacgccg | cgtgagcgaa | gaaggtcttc | ggatcgtaaa | 420 |
| gctctgttgt | cagggaagaa | caagtaccgt | tcgaacaggg | cggtaccttg | acggtacctg | 480 |
| acgaggaagc | cacggctaac | tacgtgccag | cagccgcggt | aatacgtagg | tggcaagcgt | 540 |
| tgtccggaat | tattgggcgt | aaagcgcgcg | caggcggctc | cttaagtctg | atgtgaaatc | 600 |
| tcgcggctca | accgcgagcg | gccattggaa | actggggaac | ttgagtgcag | gagaggggag | 660 |
| cggaattcca | cgtgtagcgg | tgaaatgcgt | agagatgtgg | aggaacacca | gtggcgaagg | 720 |
| cggctctctg | gcctgtaact | gacgctgagg | cgcgaaagcg | tggggagcga | acaggattag | 780 |
| ataccctggt | agtccacgcc | gtaaacgatg | agtgctaagt | gttagagggt | atccacccct | 840 |
| tagtgctgca | gcaaacgcat | taagcactcc | gcctggggag | tacggccgca | aggctgaaac | 900 |
| tcaaaggaat | tgacggggac | ccgcacaagc | ggtggagcat | gtggtttaat | tcgaagcaac | 960 |
| gcgaagaacc | ttaccaggtc | ttgacatccc | ctgacaaccc | tagagatagg | gcgttcccct | 1020 |
| ttcgggggga | cagggtgaca | ggtggtgcat | ggttgtcgtc | agctcgtgtc | gtgagatgtt | 1080 |
| gggttaagtc | ccgcaacgag | cgcaacccct | taccttagtt | gccagcattc | agttgggcac | 1140 |
| tctaaggtga | ctgccggcta | aaagtcgcgag | gaaggtgggg | atgacgtcaa | atcatcatgc | 1200 |
| cccttatgac | ctgggctaca | cacgtgctac | aatggcgtggt | acaaagggca | gcgaaaccgc | 1260 |
| gaggtggagc | gaatcccaaa | aaaccactct | cagttcggat | tgcaggctgc | aactcgcctg | 1320 |
| catgaagccg | gaatcgctag | taatcgcgga | tcagcatgcc | gcggtgaata | cgttcccggg | 1380 |
| tcttgtacac | accgcccgtc | acaccacgag | agtttgtaac | acccgaagtc | ggtggggtaa | 1440 |
| cccttacggg | agccagccgc | cgaaggtggg | acaaatgatt | ggggtgaagt | cgtaacaagg | 1500 |
| tagccgtatc | ggaaggt | | | | | 1517 |

<210> SEQ ID NO 3
<211> LENGTH: 1516
<212> TYPE: DNA
<213> ORGANISM: Bacillus pallidus
<220> FEATURE:
<221> NAME/KEY: rRNA
<222> LOCATION: (1)..(1516)
<300> PUBLICATION INFORMATION:
<308> DATABASE ACCESSION NUMBER: Z26930/GenBank
<309> DATABASE ENTRY DATE: 1997-05-14

<400> SEQUENCE: 3

| | | | | | |
|---|---|---|---|---|---|
| ctcaggacga | acgctggcgg | cgtgcctaat | acatgcaagt | cgagcggacc | gaagggagct | 60 |
| tgctccttta | ggttaacggc | ggacgggtga | gtaacacgtg | gcaacctgcc | ctgcagact | 120 |
| gggataactt | cgggaaaccg | gagctaatac | cggataacac | cgaaaccgc | atggttttcg | 180 |
| gttgaaaggc | ggcttttagc | tgtcactgca | ggatgggccc | gcggcgcatt | agctagttgg | 240 |
| tgaggtaacg | gctcaccaag | gcgacgatgc | gtagccgacc | tgagagggtg | accggccaca | 300 |

```
ctgggactga gacacggccc agactcctac gggaggcagc agtagggaat cttccgcaat     360
ggacgaaagt ctgacggagc aacgccgcgt gagcgaagaa ggtcttcgga tcgtaaagct     420
ctgttgtcag gaagaacaa gtgccgttcg aacagggcgg taccttgacg gtacctgacg      480
aggaagccac ggctaactac gtgccagcag ccgcggtaat acgtaggtgg caagcgttgt     540
ccggaattat tgggcgtaaa gcgcgcgcag gcggctcctt aagtctgatg tgaaatctcg     600
cggctcaacc gcgagcggcc attggaaact ggggaacttg agtgcaggag aggggagcgg     660
aattccacgt gtagcggtga atgcgtaga gatgtggagg aacaccagtg gcgaaggcgg     720
ctctctggcc tgtaactgac gctgaggcgc gaaagcgtgg ggagcgaaca ggattagata     780
ccctggtagt ccacgccgta aacgatgagt gctaagtgtt agagggtatc cacccttag     840 tgctgcagca aacgcattaa gcactccgcc tggggagtac ggccgcaagg ctgaaactca     900
aaggaattga cggggacccg cacaagcggt ggagcatgtg gtttaattcg aagcaacgcg     960 aagaaccta ccaggtcttg acatccctg acaaccctag atagggcg ttcccctttc        1020 ggggacaggt tgacaggtgg tgcatggttg tcgtcagctc gtgtcgtgag atgttgggtt    1080
aagtcccgca acgagcgcaa cccttgacct tagttgccag cattcagttg ggcactctaa    1140
ggtgactgcc ggctaaaagt cggaggaagg tggggatgac gtcaaatcat catgcccctt    1200
atgacctggg ctacacacgt gctacaatgg gtggtacaaa gggcagcgaa accgcgaggt    1260
ggagcgaatc ccaaaaaacc actctcagtt cggattgcag gctgcaactc gcctgcatga    1320
agccggaatc gctagtaatc gcggatcagc atgccgcggt gaatacgttc ccgggtcttg    1380
tacacaccgc ccgtcacacc acgagagttt gtaacacccg aagtcggtgg ggtaacccctt   1440 acgggagcca gccgccgaag gtgggacaaa tgattggggt gaagtcgtaa caaggtagcc    1500
gtatcggaag gtgcgg                                                     1516

<210> SEQ ID NO 4
<211> LENGTH: 497
<212> TYPE: DNA
<213> ORGANISM: Bacillus smithii
<220> FEATURE:
<221> NAME/KEY: rRNA
<222> LOCATION: (1)..(497)
<223> OTHER INFORMATION: nucleotides 17 - 513 of rRNA sequence
      X60643/Genbank
<300> PUBLICATION INFORMATION:
<308> DATABASE ACCESSION NUMBER: X60643/Genbank
<309> DATABASE ENTRY DATE: 1997-04-03

<400> SEQUENCE: 4
ctcaggacga acgctggcgg cgtgcctaat acatgcaagt cgagcggact ttcaagaagc      60 ttgcttttg aaagttagcg gcggacgggt gagtaacacg tgggcaacct gcctgcaaga     120
cggggataac tccggaaac cggggctaat accggataat atcttccttc gcatgaagga     180
aggttgaaag cggcaactgc cgcttgcaga tgggcccgcg gcgcattagc tagttggtga     240
ggtaacggct caccaaggcg acgatgcgta gccgacctga gaggtgatc ggccacactg      300 ggactgagac acggcccaga ctcctacggg aggcagcagt agggaatctt ccgcaatgga    360
cgaaagtctg acgagcaac gccgcgtgag cgaagaaggt cttcggatcg taaagctctg    420
ttgtcaggga agaacaagta ccgttcgaac agggcggtac cttgacggta cctgaccaga    480
aagccacggc taactac                                                   497

<210> SEQ ID NO 5
```

-continued

```
<211> LENGTH: 3299
<212> TYPE: DNA
<213> ORGANISM: BR449
<220> FEATURE:
<221> NAME/KEY: gene
<222> LOCATION: (432)..(1475)
<223> OTHER INFORMATION: Amidase gene
<221> NAME/KEY: gene
<222> LOCATION: (1606)..(2292)
<223> OTHER INFORMATION: Nitrile hydratase beta subunit
<221> NAME/KEY: gene
<222> LOCATION: (2321)..(2962)
<223> OTHER INFORMATION: Nitrile hydratase alpha subunit
<221> NAME/KEY: gene
<222> LOCATION: (2981)..(3283)
<223> OTHER INFORMATION: ORF 1

<400> SEQUENCE: 5
tttaactagg tgttataggg agaaaaaatt tatataggtt tacaaaaaag ggcattccta      60
tttatctttt ctacatcaat ttgaaaggga ttattgtgct ttaaatagtg cgaattttct    120
tgaaatattt tcgttctcac gttctatatt ttttaccttt taaaaaatca ttaataaatg    180
caatcatcct atctttactt cttagtcttc aaacagcgtg aaccactaat agagcttctt    240
ttaactttt catatgatga tgtgatgccg ccagacatac ttaaaaacta tgcattgatt     300
catttagaca ttctttaaga gaaaatagtt agatttaaag gaggtgatgc ctggggaaat    360
cgaacagcag gtctatatat tattatattt aattcacttc caacatttta taacaaaagg    420
aggaaaaagg catgagacac ggggatattt caagcagcca cgacacagta ggaatagcgg    480
tggtcaatta caaaatgccg cgtttgcaca cgaaagcaga agttattgaa atgcaaaaa     540
agatcgctga catggtcgta gggatgaagc aaggtcttcc aggtatggat ctcgtcgttt    600
tcccggagta cagcacaatg ggaattatgt acgatcagga tgaaatgttt gccactgcag    660
cttccatacc aggagaggaa acagctatct ttgctgaagc gtgcaaaaag gctgatacat    720
gggggggtatt ctcactaacc ggggaaaaac atgaagatca tccgaataag gcaccataca    780
acaccctagt tctcattaat aacaaaggag agattgtgca aaagtaccgc aagattattc    840
cttggtgtcc gatcgaagga tggtatccgg gagataccac ttatgtcacg gaaggaccga    900
aggggttgaa aatcagtctc atcgtttgtg atgacggaaa ttatcctgaa atctggcgcg    960
attgtgcgat gaaaggcgca gaattgatcg tccgttgcca aggctacatg tatccggcaa   1020
aagagcagca aatcatgatg gcgaaagcta tggcttgggc gaacaatacc tatgtagccg   1080
ttgccaacgc aacaggattt gacggagttt attcatattt tggccactct gccatcatcg   1140
gttttgacgg acgcacacta ggtgagtgcg gaacggagga gaatggtata cagtacgcag   1200
aagtgtccat ctctcagatt cgtgattta gaaagaacgc ccagtcccaa aatcatttgt    1260
tcaagctgct tcaccgaggc tatactggct tgatcaactc cggagaaggc gaccgaggcg   1320
tagcagaatg cccatttgat ttttatcgca cttgggtact cgatgcagaa aaggcaagag   1380
aaaatgtaga gaagatcact agaagtacgg ttgggacagc agaatgtccg attcaaggaa   1440
tcccaaatga aggaaaaaca aaagaaattg gtgtgtaatt ctggaatacc aattgtttaa   1500
tgcacaataa ctgcattttc gtcattttcc ttaagtgtta aatgagatga ctaacatatg   1560
tcatcggtaa aaataaattc ttaatcaaag atggaggta aacaaatgaa cggtattcat    1620
gatgttggag gcatggatgg atttggaaaa gtgatgtatg taaaagaaga gaggacatt    1680
tattttacac atgattggga aagacttgcg ttcggacttg tagctggttg tatggcacaa   1740
ggattgggga tgaaggcttt tgatgaattc aggatcggca ttgagcttat gcgtccagtg   1800
```

-continued

```
gattatttga cgtcgtcgta ttatggccat tggattgcaa ctgttgcata caacttagta    1860
gatacgggag tattagacga aaaagaacta gatgaacgaa cggaggtttt cttgaagaaa    1920
cctgatacca aaataccacg aagagaggat ccggcattag tgaagcttgt agaaaaggca    1980
ctgtatgaag gcttatctcc gatccgtgaa atttcagctt ctcctcggtt taaggtagga    2040
gagagaatca agacgaaaaa cattcatcca actggtcata cgagattccc tcgatatgcc    2100
cgtgacaaat atggtgtcat tgatgagata tatggagctc atgttttccc tgatgatgct    2160
gctcatagaa aaggagaaaa cccgcaatat ctttaccggg tacgttttga ggctgaagaa    2220
ttatggggat ataaacagaa agattccgtt tatatagatc tatgggaaag ttatatggag    2280
cctgtttcac attaatcatt ttttgaagga ggaatacaat atgacgattg atcaaaaaaa    2340
tactaatata gatccaagat tccacatca tcatccgcgt ccacaatcat tttgggaggc    2400
acgtgcaaaa gctcttgaat ccttgttgat tgagaaaggg catctttcct cagatgctat    2460
tgaaagggta ataaaacatt atgagcatga gctgggacca atgaacggag caaaggtcgt    2520
agcgaaggct tggactgatc ctgcttttaa acaaagattg ctagaagatc cagagactgt    2580
attaagggag ctaggatact atggtttaca gggtgagcat atcagggtag tagaaaatac    2640
ggatacggta cacaatgttg tagtctgcac tttatgttca tgttacccct ggccattgct    2700
tggtttaccg ccttcatggt acaaagaacc tgcttataga gctcgtgtcg taaaagagcc    2760
gagacaagtg ttgaaagaat tcggattaga tcttccagat tcagtagaaa tccgggtatg    2820
ggacagcagt tcagaaattc gctttatggt attgccgcaa agacctgaag gtacggaagg    2880
aatgacggag gaggagcttg caaaacttgt tactcgagac tccatgattg gtgtcgctaa    2940
aatagagccg ctaaagttac ggtaggttag gaggaaaata atgaaaagtt gtgagaatca    3000
acctaatgaa tcattgcttg cgaatatgtc tgaagaagtc gcacctccta gaaaaaacgg    3060
agagttagaa ttccaagagc cttgggaaag acgctctttt ggcatgactc ttgctttgta    3120
cgaagaaaag ctgtatagct cttgggagga ttttcgatcc cgcttgattg aggagatcaa    3180
ggggtgggag accgcgaaac agaaggagaa ttctgactgg aactactatg agcattggct    3240
ggccgccttg gaacgactag tagtggaaac aggaatgtta aattaagcgt gatgtcgac    3299
```

<210> SEQ ID NO 6
<211> LENGTH: 1044
<212> TYPE: DNA
<213> ORGANISM: BR449
<220> FEATURE:
<221> NAME/KEY: CDS
<222> LOCATION: (1)..(1044)
<223> OTHER INFORMATION: Amidase gene

<400> SEQUENCE: 6

```
atg aga cac ggg gat att tca agc agc cac gac aca gta gga ata gcg      48
Met Arg His Gly Asp Ile Ser Ser Ser His Asp Thr Val Gly Ile Ala
 1               5                  10                  15 gtg gtc aat tac aaa atg ccg cgt ttg cac acg aaa gca gaa gtt att      96
Val Val Asn Tyr Lys Met Pro Arg Leu His Thr Lys Ala Glu Val Ile
            20                  25                  30 gaa aat gca aaa aag atc gct gac atg gtc gta ggg atg aag caa ggt     144
Glu Asn Ala Lys Lys Ile Ala Asp Met Val Val Gly Met Lys Gln Gly
        35                  40                  45 ctt cca ggt atg gat ctc gtc gtt ttc ccg gag tac agc aca atg gga     192
Leu Pro Gly Met Asp Leu Val Val Phe Pro Glu Tyr Ser Thr Met Gly
    50                  55                  60 att atg tac gat cag gat gaa atg ttt gcc act gca gct tcc ata cca     240
```

```
Ile Met Tyr Asp Gln Asp Glu Met Phe Ala Thr Ala Ser Ile Pro
 65                  70                  75                  80 gga gag gaa aca gct atc ttt gct gaa gcg tgc aaa aag gct gat aca      288
Gly Glu Glu Thr Ala Ile Phe Ala Glu Ala Cys Lys Lys Ala Asp Thr
                 85                  90                  95 tgg ggg gta ttc tca cta acc ggg gaa aaa cat gaa gat cat ccg aat      336
Trp Gly Val Phe Ser Leu Thr Gly Glu Lys His Glu Asp His Pro Asn
            100                 105                 110 aag gca cca tac aac acc cta gtt ctc att aat aac aaa gga gag att      384
Lys Ala Pro Tyr Asn Thr Leu Val Leu Ile Asn Asn Lys Gly Glu Ile
        115                 120                 125 gtg caa aag tac cgc aag att att cct tgg tgt ccg atc gaa gga tgg      432
Val Gln Lys Tyr Arg Lys Ile Ile Pro Trp Cys Pro Ile Glu Gly Trp
    130                 135                 140 tat ccg gga gat acc act tat gtc acg gaa gga ccg aag ggg ttg aaa      480
Tyr Pro Gly Asp Thr Thr Tyr Val Thr Glu Gly Pro Lys Gly Leu Lys
145                 150                 155                 160 atc agt ctc atc gtt tgt gat gac gga aat tat cct gaa atc tgg cgc      528
Ile Ser Leu Ile Val Cys Asp Asp Gly Asn Tyr Pro Glu Ile Trp Arg
                165                 170                 175 gat tgt gcg atg aaa ggc gca gaa ttg atc gtc cgt tgc caa ggc tac      576
Asp Cys Ala Met Lys Gly Ala Glu Leu Ile Val Arg Cys Gln Gly Tyr
            180                 185                 190 atg tat ccg gca aaa gag cag caa atc atg atg gcg aaa gct atg gct      624
Met Tyr Pro Ala Lys Glu Gln Gln Ile Met Met Ala Lys Ala Met Ala
        195                 200                 205 tgg gcg aac aat acc tat gta gcc gtt gcc aac gca aca gga ttt gac      672
Trp Ala Asn Asn Thr Tyr Val Ala Val Ala Asn Ala Thr Gly Phe Asp
    210                 215                 220 gga gtt tat tca tat ttt ggc cac tct gcc atc atc ggt ttt gac gga      720
Gly Val Tyr Ser Tyr Phe Gly His Ser Ala Ile Ile Gly Phe Asp Gly
225                 230                 235                 240 cgc aca cta ggt gag tgc gga acg gag gag aat ggt ata cag tac gca      768
Arg Thr Leu Gly Glu Cys Gly Thr Glu Glu Asn Gly Ile Gln Tyr Ala
                245                 250                 255 gaa gtg tcc atc tct cag att cgt gat ttt aga aag aac gcc cag tcc      816
Glu Val Ser Ile Ser Gln Ile Arg Asp Phe Arg Lys Asn Ala Gln Ser
            260                 265                 270 caa aat cat ttg ttc aag ctg ctt cac cga ggc tat act ggc ttg atc      864
Gln Asn His Leu Phe Lys Leu Leu His Arg Gly Tyr Thr Gly Leu Ile
        275                 280                 285 aac tcc gga gaa ggc gac cga ggc gta gca gaa tgc cca ttt gat ttt      912
Asn Ser Gly Glu Gly Asp Arg Gly Val Ala Glu Cys Pro Phe Asp Phe
    290                 295                 300 tat cgc act tgg gta ctc gat gca gaa aag gca aga gaa aat gta gag      960
Tyr Arg Thr Trp Val Leu Asp Ala Glu Lys Ala Arg Glu Asn Val Glu
305                 310                 315                 320 aag atc act aga agt acg gtt ggg aca gca gaa tgt ccg att caa gga     1008
Lys Ile Thr Arg Ser Thr Val Gly Thr Ala Glu Cys Pro Ile Gln Gly
                325                 330                 335 atc cca aat gaa gga aaa aca aaa gaa att ggt gtg                     1044
Ile Pro Asn Glu Gly Lys Thr Lys Glu Ile Gly Val
            340                 345
```

<210> SEQ ID NO 7
<211> LENGTH: 348
<212> TYPE: PRT
<213> ORGANISM: BR449

<400> SEQUENCE: 7

| Met | Arg | His | Gly | Asp | Ile | Ser | Ser | His | Asp | Thr | Val | Gly | Ile | Ala |
|---|---|---|---|---|---|---|---|---|---|---|---|---|---|---|
| 1 | | | | 5 | | | | | 10 | | | | | 15 |

| Val | Val | Asn | Tyr | Lys | Met | Pro | Arg | Leu | His | Thr | Lys | Ala | Glu | Val | Ile |
|---|---|---|---|---|---|---|---|---|---|---|---|---|---|---|---|
| | | | 20 | | | | | 25 | | | | | 30 | | |

Glu Asn Ala Lys Lys Ile Ala Asp Met Val Val Gly Met Lys Gln Gly
            35                  40                  45

Leu Pro Gly Met Asp Leu Val Val Phe Pro Glu Tyr Ser Thr Met Gly
 50                      55                  60

Ile Met Tyr Asp Gln Asp Glu Met Phe Ala Thr Ala Ala Ser Ile Pro
 65                  70                  75                  80

Gly Glu Glu Thr Ala Ile Phe Ala Glu Ala Cys Lys Lys Ala Asp Thr
                85                  90                  95

Trp Gly Val Phe Ser Leu Thr Gly Glu Lys His Glu Asp His Pro Asn
                100                 105                 110

Lys Ala Pro Tyr Asn Thr Leu Val Leu Ile Asn Asn Lys Gly Glu Ile
                115                 120                 125

Val Gln Lys Tyr Arg Lys Ile Ile Pro Trp Cys Pro Ile Glu Gly Trp
    130                 135                 140

Tyr Pro Gly Asp Thr Thr Tyr Val Thr Glu Gly Pro Lys Gly Leu Lys
145                 150                 155                 160

Ile Ser Leu Ile Val Cys Asp Asp Gly Asn Tyr Pro Glu Ile Trp Arg
                165                 170                 175

Asp Cys Ala Met Lys Gly Ala Glu Leu Ile Val Arg Cys Gln Gly Tyr
                180                 185                 190

Met Tyr Pro Ala Lys Glu Gln Gln Ile Met Met Ala Lys Ala Met Ala
                195                 200                 205

Trp Ala Asn Asn Thr Tyr Val Ala Val Ala Asn Ala Thr Gly Phe Asp
    210                 215                 220

Gly Val Tyr Ser Tyr Phe Gly His Ser Ala Ile Ile Gly Phe Asp Gly
225                 230                 235                 240

Arg Thr Leu Gly Glu Cys Gly Thr Glu Glu Asn Gly Ile Gln Tyr Ala
                245                 250                 255

Glu Val Ser Ile Ser Gln Ile Arg Asp Phe Arg Lys Asn Ala Gln Ser
                260                 265                 270

Gln Asn His Leu Phe Lys Leu Leu His Arg Gly Tyr Thr Gly Leu Ile
    275                 280                 285

Asn Ser Gly Glu Gly Asp Arg Gly Val Ala Glu Cys Pro Phe Asp Phe
    290                 295                 300

Tyr Arg Thr Trp Val Leu Asp Ala Glu Lys Ala Arg Glu Asn Val Glu
305                 310                 315                 320

Lys Ile Thr Arg Ser Thr Val Gly Thr Ala Glu Cys Pro Ile Gln Gly
                325                 330                 335

Ile Pro Asn Glu Gly Lys Thr Lys Glu Ile Gly Val
                340                 345

```
<210> SEQ ID NO 8
<211> LENGTH: 642
<212> TYPE: DNA
<213> ORGANISM: BR449
<220> FEATURE:
<221> NAME/KEY: CDS
<222> LOCATION: (1)..(642)
<223> OTHER INFORMATION: Nitrile hydratase alpha subunit

<400> SEQUENCE: 8 atg acg att gat caa aaa aat act aat ata gat cca aga ttt cca cat         48
```

```
Met Thr Ile Asp Gln Lys Asn Thr Asn Ile Asp Pro Arg Phe Pro His
 1               5                  10                  15 cat cat ccg cgt cca caa tca ttt tgg gag gca cgt gca aaa gct ctt        96
His His Pro Arg Pro Gln Ser Phe Trp Glu Ala Arg Ala Lys Ala Leu
             20                  25                  30 gaa tcc ttg ttg att gag aaa ggg cat ctt tcc tca gat gct att gaa       144
Glu Ser Leu Leu Ile Glu Lys Gly His Leu Ser Ser Asp Ala Ile Glu
         35                  40                  45 agg gta ata aaa cat tat gag cat gag ctg gga cca atg aac gga gca       192
Arg Val Ile Lys His Tyr Glu His Glu Leu Gly Pro Met Asn Gly Ala
     50                  55                  60 aag gtc gta gcg aag gct tgg act gat cct gct ttt aaa caa aga ttg       240
Lys Val Val Ala Lys Ala Trp Thr Asp Pro Ala Phe Lys Gln Arg Leu
 65                  70                  75                  80 cta gaa gat cca gag act gta tta agg gag cta gga tac tat ggt tta       288
Leu Glu Asp Pro Glu Thr Val Leu Arg Glu Leu Gly Tyr Tyr Gly Leu
                 85                  90                  95 cag ggt gag cat atc agg gta gta gaa aat acg gat acg gta cac aat       336
Gln Gly Glu His Ile Arg Val Val Glu Asn Thr Asp Thr Val His Asn
            100                 105                 110 gtt gta gtc tgc act tta tgt tca tgt tac cct tgg cca ttg ctt ggt       384
Val Val Val Cys Thr Leu Cys Ser Cys Tyr Pro Trp Pro Leu Leu Gly
        115                 120                 125 tta ccg cct tca tgg tac aaa gaa cct gct tat aga gct cgt gtc gta       432
Leu Pro Pro Ser Trp Tyr Lys Glu Pro Ala Tyr Arg Ala Arg Val Val
    130                 135                 140 aaa gag ccg aga caa gtg ttg aaa gaa ttc gga tta gat ctt cca gat       480
Lys Glu Pro Arg Gln Val Leu Lys Glu Phe Gly Leu Asp Leu Pro Asp
145                 150                 155                 160 tca gta gaa atc cgg gta tgg gac agc agt tca gaa att cgc ttt atg       528
Ser Val Glu Ile Arg Val Trp Asp Ser Ser Ser Glu Ile Arg Phe Met
                165                 170                 175 gta ttg ccg caa aga cct gaa ggt acg gaa gga atg acg gag gag gag       576
Val Leu Pro Gln Arg Pro Glu Gly Thr Glu Gly Met Thr Glu Glu Glu
            180                 185                 190 ctt gca aaa ctt gtt act cga gac tcc atg att ggt gtc gct aaa ata       624
Leu Ala Lys Leu Val Thr Arg Asp Ser Met Ile Gly Val Ala Lys Ile
        195                 200                 205 gag ccg cta aag tta cgg                                               642
Glu Pro Leu Lys Leu Arg
    210
```

<210> SEQ ID NO 9
<211> LENGTH: 214
<212> TYPE: PRT
<213> ORGANISM: BR449

<400> SEQUENCE: 9

```
Met Thr Ile Asp Gln Lys Asn Thr Asn Ile Asp Pro Arg Phe Pro His
 1               5                  10                  15

His His Pro Arg Pro Gln Ser Phe Trp Glu Ala Arg Ala Lys Ala Leu
             20                  25                  30

Glu Ser Leu Leu Ile Glu Lys Gly His Leu Ser Ser Asp Ala Ile Glu
         35                  40                  45

Arg Val Ile Lys His Tyr Glu His Glu Leu Gly Pro Met Asn Gly Ala
     50                  55                  60

Lys Val Val Ala Lys Ala Trp Thr Asp Pro Ala Phe Lys Gln Arg Leu
 65                  70                  75                  80

Leu Glu Asp Pro Glu Thr Val Leu Arg Glu Leu Gly Tyr Tyr Gly Leu
```

```
                         85                  90                  95
Gln Gly Glu His Ile Arg Val Val Glu Asn Thr Asp Thr Val His Asn
                100                 105                 110
Val Val Val Cys Thr Leu Cys Ser Cys Tyr Pro Trp Pro Leu Leu Gly
                115                 120                 125
Leu Pro Pro Ser Trp Tyr Lys Glu Pro Ala Tyr Arg Ala Arg Val Val
            130                 135                 140
Lys Glu Pro Arg Gln Val Leu Lys Glu Phe Gly Leu Asp Leu Pro Asp
145                 150                 155                 160
Ser Val Glu Ile Arg Val Trp Asp Ser Ser Glu Ile Arg Phe Met
                    165                 170                 175
Val Leu Pro Gln Arg Pro Glu Gly Thr Glu Gly Met Thr Glu Glu
                180                 185                 190
Leu Ala Lys Leu Val Thr Arg Asp Ser Met Ile Gly Val Ala Lys Ile
                195                 200                 205
Glu Pro Leu Lys Leu Arg
            210

<210> SEQ ID NO 10
<211> LENGTH: 687
<212> TYPE: DNA
<213> ORGANISM: BR449
<220> FEATURE:
<221> NAME/KEY: CDS
<222> LOCATION: (1)..(687)
<223> OTHER INFORMATION: Nitrile hydratase beta subunit

<400> SEQUENCE: 10 atg aac ggt att cat gat gtt gga ggc atg gat gga ttt gga aaa gtg     48
Met Asn Gly Ile His Asp Val Gly Gly Met Asp Gly Phe Gly Lys Val
  1               5                  10                  15 atg tat gta aaa gaa gaa gag gac att tat ttt aca cat gat tgg gaa     96
Met Tyr Val Lys Glu Glu Glu Asp Ile Tyr Phe Thr His Asp Trp Glu
                 20                  25                  30 aga ctt gcg ttc gga ctt gta gct ggt tgt atg gca caa gga ttg ggg    144
Arg Leu Ala Phe Gly Leu Val Ala Gly Cys Met Ala Gln Gly Leu Gly
             35                  40                  45 atg aag gct ttt gat gaa ttc agg atc ggc att gag ctt atg cgt cca    192
Met Lys Ala Phe Asp Glu Phe Arg Ile Gly Ile Glu Leu Met Arg Pro
         50                  55                  60 gtg gat tat ttg acg tcg tcg tat tat ggc cat tgg att gca act gtt    240
Val Asp Tyr Leu Thr Ser Ser Tyr Tyr Gly His Trp Ile Ala Thr Val
 65                  70                  75                  80 gca tac aac tta gta gat acg gga gta tta gac gaa aaa gaa cta gat    288
Ala Tyr Asn Leu Val Asp Thr Gly Val Leu Asp Glu Lys Glu Leu Asp
                 85                  90                  95 gaa cga acg gag gtt ttc ttg aag aaa cct gat acc aaa ata cca cga    336
Glu Arg Thr Glu Val Phe Leu Lys Lys Pro Asp Thr Lys Ile Pro Arg
            100                 105                 110 aga gag gat ccg gca tta gtg aag ctt gta gaa aag gca ctg tat gaa    384
Arg Glu Asp Pro Ala Leu Val Lys Leu Val Glu Lys Ala Leu Tyr Glu
        115                 120                 125 ggc tta tct ccg atc cgt gaa att tca gct tct cct cgg ttt aag gta    432
Gly Leu Ser Pro Ile Arg Glu Ile Ser Ala Ser Pro Arg Phe Lys Val
    130                 135                 140 gga gag aga atc aag acg aaa aac att cat cca act ggt cat acg aga    480
Gly Glu Arg Ile Lys Thr Lys Asn Ile His Pro Thr Gly His Thr Arg
145                 150                 155                 160 ttc cct cga tat gcc cgt gac aaa tat ggt gtc att gat gag ata tat    528
```

```
                                                                              -continued Phe Pro Arg Tyr Ala Arg Asp Lys Tyr Gly Val Ile Asp Glu Ile Tyr
                165                 170                 175 gga gct cat gtt ttc cct gat gat gct gct cat aga aaa gga gaa aac         576
Gly Ala His Val Phe Pro Asp Asp Ala Ala His Arg Lys Gly Glu Asn
            180                 185                 190 ccg caa tat ctt tac cgg gta cgt ttt gag gct gaa gaa tta tgg gga         624
Pro Gln Tyr Leu Tyr Arg Val Arg Phe Glu Ala Glu Glu Leu Trp Gly
            195                 200                 205 tat aaa cag aaa gat tcc gtt tat ata gat cta tgg gaa agt tat atg         672
Tyr Lys Gln Lys Asp Ser Val Tyr Ile Asp Leu Trp Glu Ser Tyr Met
    210                 215                 220 gag cct gtt tca cat                                                     687
Glu Pro Val Ser His
225

<210> SEQ ID NO 11
<211> LENGTH: 229
<212> TYPE: PRT
<213> ORGANISM: BR449

<400> SEQUENCE: 11

Met Asn Gly Ile His Asp Val Gly Gly Met Asp Gly Phe Gly Lys Val
 1               5                  10                  15

Met Tyr Val Lys Glu Glu Glu Asp Ile Tyr Phe Thr His Asp Trp Glu
            20                  25                  30

Arg Leu Ala Phe Gly Leu Val Ala Gly Cys Met Ala Gln Gly Leu Gly
        35                  40                  45

Met Lys Ala Phe Asp Glu Phe Arg Ile Gly Ile Glu Leu Met Arg Pro
    50                  55                  60

Val Asp Tyr Leu Thr Ser Ser Tyr Gly His Trp Ile Ala Thr Val
65                  70                  75                  80

Ala Tyr Asn Leu Val Asp Thr Gly Val Leu Asp Glu Lys Glu Leu Asp
                85                  90                  95

Glu Arg Thr Glu Val Phe Leu Lys Lys Pro Asp Thr Lys Ile Pro Arg
            100                 105                 110

Arg Glu Asp Pro Ala Leu Val Lys Leu Val Glu Lys Ala Leu Tyr Glu
        115                 120                 125

Gly Leu Ser Pro Ile Arg Glu Ile Ser Ala Ser Pro Arg Phe Lys Val
    130                 135                 140

Gly Glu Arg Ile Lys Thr Lys Asn Ile His Pro Thr Gly His Thr Arg
145                 150                 155                 160

Phe Pro Arg Tyr Ala Arg Asp Lys Tyr Gly Val Ile Asp Glu Ile Tyr
                165                 170                 175

Gly Ala His Val Phe Pro Asp Asp Ala Ala His Arg Lys Gly Glu Asn
            180                 185                 190

Pro Gln Tyr Leu Tyr Arg Val Arg Phe Glu Ala Glu Glu Leu Trp Gly
        195                 200                 205

Tyr Lys Gln Lys Asp Ser Val Tyr Ile Asp Leu Trp Glu Ser Tyr Met
    210                 215                 220

Glu Pro Val Ser His
225

<210> SEQ ID NO 12
<211> LENGTH: 303
<212> TYPE: DNA
<213> ORGANISM: BR449
<220> FEATURE:
<221> NAME/KEY: CDS
```

<222> LOCATION: (1)..(303)
<223> OTHER INFORMATION: ORF 1

<400> SEQUENCE: 12

| atg | aaa | agt | tgt | gag | aat | caa | cct | aat | gaa | tca | ttg | ctt | gcg | aat | atg | 48 |
| Met | Lys | Ser | Cys | Glu | Asn | Gln | Pro | Asn | Glu | Ser | Leu | Leu | Ala | Asn | Met | |
| 1 | | | | 5 | | | | | 10 | | | | | 15 | | |

| tct | gaa | gaa | gtc | gca | cct | cct | aga | aaa | aac | gga | gag | tta | gaa | ttc | caa | 96 |
| Ser | Glu | Glu | Val | Ala | Pro | Pro | Arg | Lys | Asn | Gly | Glu | Leu | Glu | Phe | Gln | |
| | | | 20 | | | | | 25 | | | | | 30 | | | |

| gag | cct | tgg | gaa | aga | cgc | tct | ttt | ggc | atg | act | ctt | gct | ttg | tac | gaa | 144 |
| Glu | Pro | Trp | Glu | Arg | Arg | Ser | Phe | Gly | Met | Thr | Leu | Ala | Leu | Tyr | Glu | |
| | | 35 | | | | | 40 | | | | | 45 | | | | |

| gaa | aag | ctg | tat | agc | tct | tgg | gag | gat | ttt | cga | tcc | cgc | ttg | att | gag | 192 |
| Glu | Lys | Leu | Tyr | Ser | Ser | Trp | Glu | Asp | Phe | Arg | Ser | Arg | Leu | Ile | Glu | |
| | 50 | | | | | 55 | | | | | 60 | | | | | |

| gag | atc | aag | ggg | tgg | gag | acc | gcg | aaa | cag | aag | gag | aat | tct | gac | tgg | 240 |
| Glu | Ile | Lys | Gly | Trp | Glu | Thr | Ala | Lys | Gln | Lys | Glu | Asn | Ser | Asp | Trp | |
| 65 | | | | 70 | | | | | 75 | | | | | 80 | | |

| aac | tac | tat | gag | cat | tgg | ctg | gcc | gcc | ttg | gaa | cga | cta | gta | gtg | gaa | 288 |
| Asn | Tyr | Tyr | Glu | His | Trp | Leu | Ala | Ala | Leu | Glu | Arg | Leu | Val | Val | Glu | |
| | | | 85 | | | | | 90 | | | | | 95 | | | |

| aca | gga | atg | tta | aat | | | | | | | | | | | | 303 |
| Thr | Gly | Met | Leu | Asn | | | | | | | | | | | | |
| | | | 100 | | | | | | | | | | | | | |

<210> SEQ ID NO 13
<211> LENGTH: 101
<212> TYPE: PRT
<213> ORGANISM: BR449

<400> SEQUENCE: 13

Met Lys Ser Cys Glu Asn Gln Pro Asn Glu Ser Leu Leu Ala Asn Met
1               5                   10                  15

Ser Glu Glu Val Ala Pro Pro Arg Lys Asn Gly Glu Leu Glu Phe Gln
            20                  25                  30

Glu Pro Trp Glu Arg Arg Ser Phe Gly Met Thr Leu Ala Leu Tyr Glu
        35                  40                  45

Glu Lys Leu Tyr Ser Ser Trp Glu Asp Phe Arg Ser Arg Leu Ile Glu
    50                  55                  60

Glu Ile Lys Gly Trp Glu Thr Ala Lys Gln Lys Glu Asn Ser Asp Trp
65                  70                  75                  80

Asn Tyr Tyr Glu His Trp Leu Ala Ala Leu Glu Arg Leu Val Val Glu
                85                  90                  95

Thr Gly Met Leu Asn
            100

<210> SEQ ID NO 14
<211> LENGTH: 660
<212> TYPE: DNA
<213> ORGANISM: Bacillus smithii
<220> FEATURE:
<221> NAME/KEY: mat_peptide
<222> LOCATION: (4)..(660)
<223> OTHER INFORMATION: Nitrile hydratase alpha subunit
<221> NAME/KEY: CDS
<222> LOCATION: (1)..(660)
<223> OTHER INFORMATION: Nitrile hydratase alpha subunit
<300> PUBLICATION INFORMATION:
<308> DATABASE ACCESSION NUMBER: E13931/GenBank
<309> DATABASE ENTRY DATE: 1997-05-14

<400> SEQUENCE: 14

```
atg gca att gaa caa aaa ttg atg gat gat cat cat gaa gtg gat ccg      48
Met Ala Ile Glu Gln Lys Leu Met Asp Asp His His Glu Val Asp Pro
 -1   1               5                  10                  15 cga ttt cca cat cat cat ccc cgg ccg caa tcg ttt tgg gaa gca cgg      96
Arg Phe Pro His His His Pro Arg Pro Gln Ser Phe Trp Glu Ala Arg
                 20                  25                  30 gct aaa gcg ctt gaa tct ctg tta att gag aaa aga ctt ctt tcc tct     144
Ala Lys Ala Leu Glu Ser Leu Leu Ile Glu Lys Arg Leu Leu Ser Ser
             35                  40                  45 gac gcc att gag agg gtt ata aaa cac tat gaa cat gag ctt ggg ccg     192
Asp Ala Ile Glu Arg Val Ile Lys His Tyr Glu His Glu Leu Gly Pro
                 50                  55                  60 atg aac gga gct aaa gtc gtt gcg aag gcc tgg acc gat cct gaa ttt     240
Met Asn Gly Ala Lys Val Val Ala Lys Ala Trp Thr Asp Pro Glu Phe
 65                  70                  75 aaa caa aga ttg ctg gaa gat cca gaa act gtg ttg cgg gaa ctt gga     288
Lys Gln Arg Leu Leu Glu Asp Pro Glu Thr Val Leu Arg Glu Leu Gly
     80                  85                  90                  95 tat ttt ggt ctg caa gga gag cat atc agg gta gtg gaa aat acg gat     336
Tyr Phe Gly Leu Gln Gly Glu His Ile Arg Val Val Glu Asn Thr Asp
                100                 105                 110 acg gta cac aat gta gtg gtt tgc act cta tgt tca tgt tat cct tgg     384
Thr Val His Asn Val Val Val Cys Thr Leu Cys Ser Cys Tyr Pro Trp
                115                 120                 125 ccg ctg ctt ggt tta ccg cct tca tgg tat aaa gaa ccg gcc tac cgt     432
Pro Leu Leu Gly Leu Pro Pro Ser Trp Tyr Lys Glu Pro Ala Tyr Arg
             130                 135                 140 tct cgg gtt gtt aaa gag ccg aga aaa gta ctg caa gaa ttc gga tta     480
Ser Arg Val Val Lys Glu Pro Arg Lys Val Leu Gln Glu Phe Gly Leu
    145                 150                 155 gac ttg ccg gat tca gta gaa att cgg gtt tgg gac agt agt tca gaa     528
Asp Leu Pro Asp Ser Val Glu Ile Arg Val Trp Asp Ser Ser Ser Glu
160                 165                 170                 175 gtt cgt ttt atg gta ttg ccg caa aga cct gag ggc aca gaa gga atg     576
Val Arg Phe Met Val Leu Pro Gln Arg Pro Glu Gly Thr Glu Gly Met
                180                 185                 190 acg gag gag gag ctg gcg caa atc gtt act cgt gac tcc atg att ggc     624
Thr Glu Glu Glu Leu Ala Gln Ile Val Thr Arg Asp Ser Met Ile Gly
            195                 200                 205 gtc gcc aaa gtt cag ccg cct aaa gtg atc caa gaa                     660
Val Ala Lys Val Gln Pro Pro Lys Val Ile Gln Glu
            210                 215
```

<210> SEQ ID NO 15
<211> LENGTH: 220
<212> TYPE: PRT
<213> ORGANISM: Bacillus smithii

<400> SEQUENCE: 15

```
Met Ala Ile Glu Gln Lys Leu Met Asp Asp His His Glu Val Asp Pro
 -1   1               5                  10                  15

Arg Phe Pro His His His Pro Arg Pro Gln Ser Phe Trp Glu Ala Arg
                 20                  25                  30

Ala Lys Ala Leu Glu Ser Leu Leu Ile Glu Lys Arg Leu Leu Ser Ser
             35                  40                  45

Asp Ala Ile Glu Arg Val Ile Lys His Tyr Glu His Glu Leu Gly Pro
                 50                  55                  60

Met Asn Gly Ala Lys Val Val Ala Lys Ala Trp Thr Asp Pro Glu Phe
 65                  70                  75
```

```
Lys Gln Arg Leu Leu Glu Asp Pro Glu Thr Val Leu Arg Glu Leu Gly
 80                  85                  90                  95

Tyr Phe Gly Leu Gln Gly Glu His Ile Arg Val Val Glu Asn Thr Asp
                100                 105                 110

Thr Val His Asn Val Val Cys Thr Leu Cys Ser Cys Tyr Pro Trp
            115                 120                 125

Pro Leu Leu Gly Leu Pro Pro Ser Trp Tyr Lys Glu Pro Ala Tyr Arg
            130                 135                 140

Ser Arg Val Val Lys Glu Pro Arg Lys Val Leu Gln Glu Phe Gly Leu
        145                 150                 155

Asp Leu Pro Asp Ser Val Glu Ile Arg Val Trp Asp Ser Ser Ser Glu
160                 165                 170                 175

Val Arg Phe Met Val Leu Pro Gln Arg Pro Glu Gly Thr Glu Gly Met
                180                 185                 190

Thr Glu Glu Glu Leu Ala Gln Ile Val Thr Arg Asp Ser Met Ile Gly
                195                 200                 205

Val Ala Lys Val Gln Pro Pro Lys Val Ile Gln Glu
            210                 215
```

<210> SEQ ID NO 16
<211> LENGTH: 687
<212> TYPE: DNA
<213> ORGANISM: Bacillus smithii
<220> FEATURE:
<221> NAME/KEY: mat_peptide
<222> LOCATION: (1)..(687)
<223> OTHER INFORMATION: Nitrile hydratase beta subunit
<221> NAME/KEY: CDS
<222> LOCATION: (1)..(687)
<223> OTHER INFORMATION: Nitrile hydratase subunit
<300> PUBLICATION INFORMATION:
<308> DATABASE ACCESSION NUMBER: E13931/GenBank
<309> DATABASE ENTRY DATE: 1997-05-14

<400> SEQUENCE: 16

```
atg aat ggg att cat gat gtt ggc ggc atg gat gga ttt ggg aaa att      48
Met Asn Gly Ile His Asp Val Gly Gly Met Asp Gly Phe Gly Lys Ile
 1               5                  10                  15 atg tat gtg aaa gaa gag gaa gat act tat ttc aaa cat gat tgg gaa      96
Met Tyr Val Lys Glu Glu Glu Asp Thr Tyr Phe Lys His Asp Trp Glu
                20                  25                  30 agg ctt act ttc ggt ctt gtt gcc ggc tgc atg gct caa gga ttg gga     144
Arg Leu Thr Phe Gly Leu Val Ala Gly Cys Met Ala Gln Gly Leu Gly
            35                  40                  45 atg aag gct ttt gat gaa ttt agg att ggc att gaa aaa atg cgt cca     192
Met Lys Ala Phe Asp Glu Phe Arg Ile Gly Ile Glu Lys Met Arg Pro
        50                  55                  60 gtt gat tat ctg aca tca tcc tat tat ggt cat tgg att gca acc gtc     240
Val Asp Tyr Leu Thr Ser Ser Tyr Tyr Gly His Trp Ile Ala Thr Val
 65                  70                  75                  80 gca tac aac ttg ttg gaa acg gga gta ctg gat gaa aaa gaa ttg gaa     288
Ala Tyr Asn Leu Leu Glu Thr Gly Val Leu Asp Glu Lys Glu Leu Glu
                85                  90                  95 gat cga aca caa gct ttc atg gaa aaa ccc gac acc aaa ata caa cgt     336
Asp Arg Thr Gln Ala Phe Met Glu Lys Pro Asp Thr Lys Ile Gln Arg
            100                 105                 110 tgg gag aat ccg aaa tta gtt aag gtt gta gaa aaa gcc ctg ctt gaa     384
Trp Glu Asn Pro Lys Leu Val Lys Val Val Glu Lys Ala Leu Leu Glu
        115                 120                 125 ggt tta tct cct gtc cgt gaa gtt tcc tca ttt cca cgg ttt gag gtg     432
```

```
Gly Leu Ser Pro Val Arg Glu Val Ser Ser Phe Pro Arg Phe Glu Val
        130                 135                 140 gga gaa aga ata aag aca agg aac att cac cca aca ggc cac act aga      480
Gly Glu Arg Ile Lys Thr Arg Asn Ile His Pro Thr Gly His Thr Arg
145                 150                 155                 160 ttt cca cga tac gtg cgc gat aag tat gga gtc att gaa gag gta tat      528
Phe Pro Arg Tyr Val Arg Asp Lys Tyr Gly Val Ile Glu Glu Val Tyr
                165                 170                 175 ggg gct cat gtt ttc cct gat gac gct gct cac aga aaa gga gaa aac      576
Gly Ala His Val Phe Pro Asp Asp Ala Ala His Arg Lys Gly Glu Asn
            180                 185                 190 ccg caa tat ctc tat cgt gta cgt ttt gat gcc gaa gaa tta tgg gga      624
Pro Gln Tyr Leu Tyr Arg Val Arg Phe Asp Ala Glu Glu Leu Trp Gly
        195                 200                 205 gta aaa cag aat gat tca gtt tat atc gat ctt tgg gaa ggt tat ttg      672
Val Lys Gln Asn Asp Ser Val Tyr Ile Asp Leu Trp Glu Gly Tyr Leu
210                 215                 220 gaa cct gtt tca cat                                                   687
Glu Pro Val Ser His
225
```

<210> SEQ ID NO 17
<211> LENGTH: 229
<212> TYPE: PRT
<213> ORGANISM: Bacillus smithii

<400> SEQUENCE: 17

```
Met Asn Gly Ile His Asp Val Gly Gly Met Asp Gly Phe Gly Lys Ile
1               5                   10                  15

Met Tyr Val Lys Glu Glu Asp Thr Tyr Phe Lys His Asp Trp Glu
            20                  25                  30

Arg Leu Thr Phe Gly Leu Val Ala Gly Cys Met Ala Gln Gly Leu Gly
        35                  40                  45

Met Lys Ala Phe Asp Glu Phe Arg Ile Gly Ile Glu Lys Met Arg Pro
    50                  55                  60

Val Asp Tyr Leu Thr Ser Ser Tyr Tyr Gly His Trp Ile Ala Thr Val
65                  70                  75                  80

Ala Tyr Asn Leu Leu Glu Thr Gly Val Leu Asp Glu Lys Glu Leu Glu
                85                  90                  95

Asp Arg Thr Gln Ala Phe Met Glu Lys Pro Asp Thr Lys Ile Gln Arg
            100                 105                 110

Trp Glu Asn Pro Lys Leu Val Lys Val Glu Lys Ala Leu Leu Glu
        115                 120                 125

Gly Leu Ser Pro Val Arg Glu Val Ser Ser Phe Pro Arg Phe Glu Val
    130                 135                 140

Gly Glu Arg Ile Lys Thr Arg Asn Ile His Pro Thr Gly His Thr Arg
145                 150                 155                 160

Phe Pro Arg Tyr Val Arg Asp Lys Tyr Gly Val Ile Glu Glu Val Tyr
                165                 170                 175

Gly Ala His Val Phe Pro Asp Asp Ala Ala His Arg Lys Gly Glu Asn
            180                 185                 190

Pro Gln Tyr Leu Tyr Arg Val Arg Phe Asp Ala Glu Glu Leu Trp Gly
        195                 200                 205

Val Lys Gln Asn Asp Ser Val Tyr Ile Asp Leu Trp Glu Gly Tyr Leu
210                 215                 220

Glu Pro Val Ser His
225
```

```
<210> SEQ ID NO 18
<211> LENGTH: 148
<212> TYPE: PRT
<213> ORGANISM: Rhodococcus rhodochrous
<300> PUBLICATION INFORMATION:
<308> DATABASE ACCESSION NUMBER: D83695
<309> DATABASE ENTRY DATE: 1997-02-25

<400> SEQUENCE: 18

Met Pro Arg Leu Asn Glu Gln Pro His Pro Gly Leu Glu Ala Asn Leu
 1               5                  10                  15

Gly Asp Leu Val Gln Asn Leu Pro Phe Asn Glu Arg Ile Pro Arg Arg
                20                  25                  30

Ser Gly Glu Val Ala Phe Asp Gln Ala Trp Glu Ile Arg Ala Phe Ser
            35                  40                  45

Ile Ala Thr Ala Leu His Gly Gln Gly Arg Phe Glu Trp Asp Glu Phe
        50                  55                  60

Gln Ser Arg Leu Ile Glu Ser Ile Lys Gln Trp Glu Ala Glu His Ala
 65                  70                  75                  80

Thr Thr Glu Gln Trp Ser Tyr Tyr Glu Arg Trp Met Leu Ala Leu Glu
                85                  90                  95

Glu Leu Leu His Asp Lys Gly Phe Val Ala Gly Glu Glu Leu Ala His
               100                 105                 110

Arg Thr Glu Gln Val Leu Ala Thr Pro Ala Gly Ala His His Gln His
           115                 120                 125

Ala Val Arg Asp Pro Ile Ala Val His Ala Ile Gly Thr Arg Thr Thr
       130                 135                 140

Asp Ser Asp Gly
145
```

METHOD FOR PRODUCING AMIDE COMPOUNDS USING A NITRILE HYDRATASE FROM A THERMOPHILIC BACILLUS

CROSS-REFERENCE TO RELATED APPLICATIONS

This application is a divisional application of Ser. No. 09/248,528, filed Feb. 10, 1999, now patented, U.S. Pat. No. 6,153,415.

This application claims the benefit of U.S. Provisional Application Serial No. 60/083,485 which was filed Apr. 29, 1998.

BACKGROUND OF THE INVENTION (1) Field of the Invention

The present invention relates to a novel nitrile hydratase and the DNA encoding the nitrile hydratase, from a thermophilic Bacillus sp., which is constitutively expressed, activated in the presence of cobalt ions, active within a temperature range of 5° C. to 70° C. and a pH range of 5 to 9, and stable at elevated temperatures of 50° C. to 60° C. in the presence of acrylonitrile for a significant period of time. Further, the present invention relates to the use of the nitrile hydratase to produce acrylamide which is used for forming polymers.

(2) Description of Related Art

Enzymatic formation of acrylamide from acrylonitrile offers advantages over the traditional copper-catalyzed process in reduction of unwanted waste products and decreased energy input, making the process a promising example of utilization of enzymes for development of "green" processes for commodity chemical production (Ashina, Y., et al., in Industrial Applications of Immobilized Biocatalysts, A. Tanaka, T. Tosa, T. Kobayashi, eds. Marcell Dekker, N.Y. p. 91–107 (1993)). Nitrile hydratases capable of catalyzing this hydration have been found in a wide variety of bacteria (Yamada, H., et al., Biosci. Biotech. Biochem. 60:1391–1400 (1996); and Cramp, R., et al., Microbiology 143:2313–2320 (1997)). Nitto Chemical Company, Japan, has pioneered the utilization of the nitrile hydratase from *Rhodococcus rhodochrous* J1 for the production of acrylamide from acrylonitrile. The *R. rhodochrous* nitrile hydratase is a novel enzyme which contains cobalt bound at the active site. The cobalt ion containing nitrile hydratases provide more attractive catalytic features than ferric ion-containing nitrile hydratases (Nagasawa, T., et al., Appl. Microbiol. Biotechnol. 40:189–195 (1993)). Although the Nitto acrylamide process is in successful production, their bioconversion process uses immobilized non-viable whole cells in the process which is run at a temperature below 10° C. and with modest acrylonitrile concentrations in order to prevent inactivation of the hydratase enzyme catalyst by the acrylonitrile substrate and to avoid product polymerization (Nagasawa, T., et al., Appl. Microbiol. Biotechnol. 40:189–195 (1993)).

U.S. Pat. No. 4,001,081 to Commeyras et al describes the use of various mesophilic bacterial species from the genus Bacteridium (in the sense of Prevot), genus Micrococcus (in the sense of Bergey), genus Bacillus and genus Brevibacterium (in the sense of Bergey) for conversion of nitriles to amides. In particular, the strain R 332, a mesophilic Bacillus species, was cited as having nitrilasic activity. R332 was shown to have optimal growth between 20° C. and 40° C. (see U.S. Pat. No. 5,563,053 to Takashima et al). In the nitrilasic reaction with any of the above bacteria, the pH is maintained at the pH value which is limiting for the hydrolysis of the amide to its acid. The reaction temperature is 25° C.

U.S. Pat. No. 4,248,968 to Watanabe et al describes a process to convert acrylonitrile to acrylamide by using bacteria strains from either Corynebacterium or Nocardia genera. However, bacteria from genus Bacillus, genus Bacteridium, and genus Brevibacterium were also recited as being useful. The nitrile hydratase described has high activity but has low heat resistance and is inactivated in a rather short time period at temperatures between 25° C. and 30° C. Therefore, while the reactions are performed between 0° and 30° C., the reactions are preferably performed at 15° C. or less.

U.S. Pat. No. 4,629,700 to Prevatt et al relates to conversion of aromatic polynitriles having no hydroxyl groups to an aromatic compound having at least one cyano group and one amide group or acid group. The invention discloses Rhodococcus species which have nitrilase systems capable of selectively hydrolyzing various cyano groups of the polynitrile. The nitrilase systems are induced either prior to or simultaneously with conversion of the aromatic polynitrile. The conversion of a dinitrile to a nitrile amide according to the invention is performed within the temperature range of 15° C. to 35° C.

U.S. Pat. No. 4,637,982 to Yamada et al relates to a process which uses various Pseudomonas species to cause the conversion of a nitrile to its corresponding amide. The process is performed under alkaline conditions at a temperature between the range of 0° to 20° C. The cells prior to use in the process are cultivated in the presence of an inducer (e.g., isobutyronitrile in the case when acrylonitrile is to be hydrated).

U.S. Pat. No. 5,130,235 to Beppu et al describes isolated DNA of Rhodococcus sp. N-774 encoding nitrile hydratase activity and recombinant *E. coli* containing the DNA. The nitrile hydratase activity appears to require $Fe^+$ ions. A method for producing the nitrile hydratase in culture medium is also disclosed.

U.S. Pat. No. 5,135,858 to Yamada et al describes a *Rhodococcus rhodochrous* strain J-1. wherein a lactam induces the nitrilase activity in the cultured strain which is then used for the conversion of a nitrile to its corresponding acid. The conversion process is performed under temperatures ranging from 5° to 50° C. and within a pH between 4 and 10.

U.S. Pat. No. 5,334,519 to Yamada et al describes the use of cobalt cores with *Rhodococcus rhodochrous* strain J-1 to enhance the action of the nitrile hydratase in the conversion of a nitrile to its corresponding amide. In particular, the bacteria is cultivated in culture medium containing cobalt ions and a nitrile or amide inducer to induce the nitrile hydratase. The bacteria is then used for the conversion process which is performed at a temperature between 15° C. to 50° C. and a pH that is usually between 7 to 9.

U.S. Pat. No. 5,563,053 to Takashima et al describes a process for production of amide compounds from their nitrile precursor using the thermophilic bacterium *Bacillus smithii* strain SC-J05-1. The nitrile hydratase activity is inducible when a nitrile compound or an amide compound is added to the culture medium. The useful temperature range for the conversion process is between 0° C. and 70° C.

The foregoing provide attractive methods for production of an amide. from its corresponding nitrile, in particular acrylamide from acrylonitrile. However, utilization of many of these nitrile hydratase enzymes has been limited by the requirement that very low temperatures be used for the bioconversion conditions, which increases production costs by requiring the reactions to be cooled.

SUMMARY OF THE INVENTION

The present invention provides novel thermophilic strains of Bacillus sp. which have a constitutive and non-inducible nitrile hydratase activity and a relatively low amidase activity which is useful for conversion of a nitrile to an amide without producing significant amounts of the corresponding acid. In particular, the present invention relates to the conversion of acrylonitrile to acrylamide by the thermophilic Bacillus sp. BR449. The nitrile hydratase of Bacillus sp. BR449 has high activity at temperatures between 20° C. and 70° C. and in the presence of relatively high concentrations of the nitrile. Importantly, the nitrile hydratase has maximal activity at 55° C. and is stable at temperatures up to 60° C. The hydratase activity is stimulated by cultivating the bacterium in media supplemented with divalent metal ions, particularly cobalt ions.

The present invention also provides a process for the bioconversion of a nitrile to its corresponding amide with little production of the corresponding acid. The bioconversion process uses the nitrile hydratase activity of the novel thermophilic Bacillus sp. BR449. In particular, the bioconversion of acrylonitrile to acrylamide is described.

Objects

It is therefore an object of the present invention to provide thermophilic strains of bacteria such as the Bacillus sp. disclosed herein which produces a nitrile hydratase that is active at temperatures between 20° C. to 70° C. and in the presence of relatively high concentrations of the nitrile wherein the nitrile hydratase converts the nitrile to its corresponding amide. In particular, the object relates to the conversion of acrylonitrile to acrylamide.

Another object of the present invention is to provide a process for producing an amide from a nitrile using the thermophilic bacteria of the invention, which comprises subjecting the nitrile in an aqueous medium to the bacterium of the present invention which has the ability to hydrolyze the acrylonitrile to acrylamide, at a temperature ranging from 20° C. to 70° C. and at a pH of about 5 to 9.

A further object of the present invention is to provide the isolated DNA from the thermophilic strain of bacterium of the present invention which encodes a nitrile hydratase, wherein the DNA is operably linked to a promoter, in a plasmid, and wherein the plasmid is stably introduced into an organism such as E. coli to produce a transformant. The transformant produces the nitrile hydratase which hydrolyzes a nitrile to produce its corresponding amide, at a temperature ranging from 20° C. to 70° C. at a pH of about 5 to 9. In particular, the object relates to the conversion of acrylonitrile to acrylamide.

An object further still of the present invention is to provide the nitrile hydratase as an isolated protein produced by the thermophilic strain of Bacillus or an organism transformed with the isolated DNA encoding the nitrile hydratase. The isolated protein is used to hydrolyze a nitrile to produce its corresponding amide, at a temperature ranging from 20° C. to 70° C. at a pH of about 5 to 9. In particular, the object relates to the conversion of acrylonitrile to acrylamide.

Thus, in view of the foregoing objects, the present invention relates to bioconversion processes that are useful for the conversion of a nitrile to its corresponding amide which is rapid and economical. In particular, the bioconversion process disclosed herein relates to the conversion of acrylonitrile to acrylamide. Other objects will become increasingly apparent by reference to the following description and the drawings.

DESCRIPTION OF THE DRAWINGS

FIG. 6 is a 16S gene sequence for BR449 (SEQ ID NO:1).

FIG. 7 is a comparison of the DNA sequence of the 16S rRNA gene of BR449 to the 16S rRNA gene of Bacillus sp13 DSM 2349 (SEQ ID NO:2).

FIG. 8 is a comparison of the DNA sequence of the 16S rRNA gene of BR449 to the 16S RNA gene of Bacillus pallidus (SEQ ID NO:3).

FIG. 9 is a comparison of the DNA sequence of the 16S rRNA gene of BR449 to the 16S rRNA gene of *Bacillus smithii* (SEQ ID NO:4).

FIG. 10 is the DNA sequence of a 3.3 kb DNA fragment from BR449 (SEQ ID NO:5) encoding the alpha subunit and beta subunit of the BR449 nitrile hydratase and an amidase gene. Also identified is open reading frame ORF1.

FIG. 11 is the amino acid sequence of the alpha subunit of the BR449 nitrile hydratase (SEQ ID NO:9).

FIG. 12 is the amino acid sequence of the beta subunit of the BR449 nitrile hydratase (SEQ ID NO:11).

FIGS. 13A and 13B are the amino acid sequence of the amidase gene (SEQ ID NO:7).

FIG. 14 is the amino acid sequence of ORF1 (SEQ ID NO:13).

FIG. 15 is a comparison of the DNA sequence of the alpha subunit of the BR449 nitrile hydratase (SEQ ID NO:8) to the DNA sequence of alpha subunit of the B. smithii strain SC-J05-1 nitrile hydratase (SEQ ID NO:14). Scoring matrix: gap penalties: −12/−2, global alignment score: 1767.

FIG. 16 is a comparison of the amino acid sequence of the alpha subunit of the BR449 nitrile hydratase (SEQ ID NO:9) to the amino acid sequence of alpha subunit of the B. smithii strain SC-J05–1 nitrile hydratase (SEQ ID NO:15). Scoring matrix: gap penalties: −12/−2, global alignment score: 1318.

FIG. 17 is a comparison of the DNA sequence of the beta subunit of the BR449 nitrile hydratase (SEQ ID NO:10) to the DNA sequence of alpha subunit of the B. smithii strain SC-J05-1 nitrile hydratase (SEQ ID NO:16). Scoring matrix: gap penalties: −12/−2, global alignment score: 1908.

FIG. 18 is a comparison of the amino acid sequence of the beta subunit of the BR449 nitrile hydratase (SEQ ID NO:11) to the amino acid sequence of alpha subunit of the B. smithii strain SC-J05-1 nitrile hydratase (SEQ ID NO:17). Scoring matrix: gap penalties: −12/−2, global alignment score: 1397.

FIG. 19 is the result of a homology search for the amino acid sequence of ORF1 (SEQ ID NO:13) showing a partial sequence identity to the nitrile hydratase beta subunit of *Rhodococcus rhodochrous* D83695 (SEQ ID NO:18).

FIG. 20 is the sequence of the 2,645 PstI/SalI DNA fragment which was shown to confer nitrile hydratase activity in *E coli* transformed with the DNA fragment. This DNA fragment is a subset of the DNA sequence (SEQ ID NO:5) shown in FIG. 10.

DETAILED DESCRIPTION OF THE INVENTION

Figure 1:
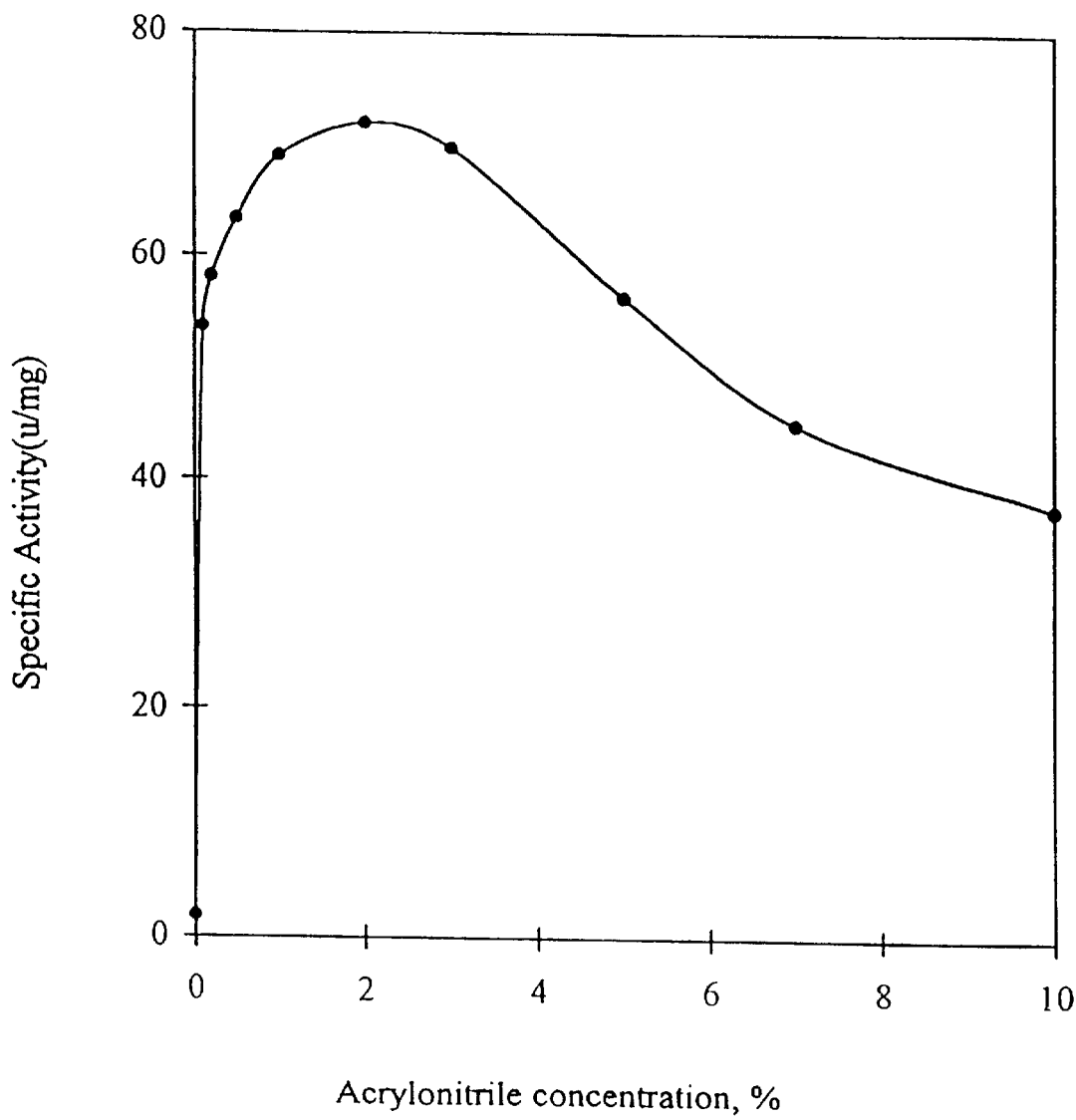
FIG. 1 is a graph showing nitrile hydratase activity with varied acrylonitrile concentration for BR449.

The present invention relates to a thermophilic strain of Bacillus which has a constitutive and non-inducible nitrile hydratase activity and relatively low amidase activity which is useful for conversion of acrylonitrile to acrylamide without producing significant amounts of acrylic acid. The nitrile hydratase activity is constitutively expressed, activated by a cobalt ion, active at temperatures between 20° C. to 70° C., stable at 60° C., and in the presence of relatively high concentrates of the acrylonitrile. The nitrile activity is useful for conversion of other nitrile compounds to the corresponding amide compounds.

Examples of other nitrile compounds of commercial interest which can be converted into its corresponding amide compounds are aliphatic nitriles such as n-butyronitrile, n-valeronitrile, isobutyronitrile, acetonitrile and pivalonitrile; halogen-containing nitrile compounds such as 2-chloropropionitrile; unsaturated aliphatic nitrile compounds such as crotononitrile and methacrylonitrile; hydroxynitrile compounds such as lactonitrile and mendelonitrile; aminonitrile compounds such as 2-phenylglycinonitrile; aromatic nitrile compounds such as benzonitrile and cyanopyridines; and dinitrile compounds such as malononitrile, succinonitrile and adiponitrile.

The present invention specifically relates to an isolated and purified thermophilic bacterial strain which has characteristics of a member of the genus Bacillus deposited as ATCC 202119. The present invention also relates to a nitrile hydratase produced by the bacterial strain deposited as ATCC 202119.

The present invention also relates to a process for producing acrylamide using a thermophilic Bacillus sp. wherein ATCC 202119 is an example, which comprises subjecting acrylonitrile in an aqueous medium to microorganisms having the ability to hydrolyze the acrylonitrile to produce acrylamide, at a temperature ranging from 20° C. to 70° C. at a pH of about 5 to 9. The conversion of acrylonitrile to acrylamide can be achieved using a broth of intact bacterial cells, disrupted bacterial cells or enzymes contained therein, or immobilized preparations obtained by immobilizing intact bacterial cells, disrupted bacterial cells or enzymes contained therein. The bacterial cells are those of a biologically pure culture of the thermophilic Bacillus sp. having nitrile hydratase activity. The nitrile hydratase produced by the Bacillus sp. is also useful for conversion of other nitrile compounds to the corresponding amide compounds. Thus, the present invention relates to a process for the conversion of a nitrile to an amide which comprises: reacting the nitrile with a thermophilic bacterium which expresses a nitrile hydratase that is active at 20° C. to 70° C.; and isolating the amide.

The present invention also relates to an isolated DNA encoding an enzyme having a nitrile hydratase activity wherein the enzyme is nitrile hydratase having at least 80% identity to the DNA sequence shown in SEQ ID NO:5 wherein nucleotide positions 1606 to 2292 encode the beta subunit of the nitrile hydratase and positions 2321 to 2962 encode the alpha subunit of the hydratase. Specifically, isolated DNAs are disclosed which encode the alpha subunit of the nitrile hydratase having at least 90% identity to the amino acid sequence shown in SEQ ID NO:9 and the beta subunit of the nitrile hydratase having at least 90% identity to the amino acid sequence shown in SEQ ID NO:11.

The present invention further relates to the isolated DNAs encoding the alpha and beta subunits of the nitrile hydratase enzyme (SEQ ID NO:8 and SEQ ID NO:10, respectively) wherein each isolated DNA is operably linked to a promoter in the same plasmid or separate plasmids. Alternatively, a single isolated DNA as shown in SEQ ID NO:5 from positions 1606 to 2662 encoding both the alpha and beta subunits in tandem wherein a single promoter is operably linked to the 5' end of the DNA at position 1606. The promoter produces a polycistronic mRNA that is translated in the bacterium into alpha and beta subunit proteins. The plasmid or plasmids encoding the alpha and beta subunits are stably introduced into an organism such as *E. coli* to produce a transformant. The cloned alpha and beta subunit genes can also be expressed from suitable expression vectors when transfected into eukaryote organisms such as yeast or plants. The transformed procaryote or eukaryote organism produces the nitrile hydratase which hydrolyzes acrylonitrile to produce acrylamide, at a temperature ranging from 20° C. to 70° C. at a pH of about 5 to 9. The nitrile hydratase produced by the transformed organism is also useful for conversion of other nitrile compounds to its corresponding amide compounds. Thus, the present invention relates to a process for making an organism useful for the conversion of a nitrile to an amide which comprises: providing an isolated DNA encoding the nitrile hydratase; introducing the isolated DNA into an organism; and using the organism to produce the nitrile hydratase.

The present invention further relates to a nitrile hydratase as an isolated protein produced by a thermophilic Bacillus sp., particularly from the Bacillus sp. BR449 deposited as ATCC 202119. The alpha subunit comprising the isolated nitrile hydratase has an amino acid sequence substantially similar to that shown in SEQ ID NO:9 and the beta subunit comprising the isolated nitrile hydratase has an amino acid sequence substantially similar to that shown in SEQ ID NO:11. The isolated protein is used to hydrolyze acrylonitrile to produce acrylamide, at a temperature ranging from 20° C. to 70° C. at a pH of about 5 to 9. The nitrile activity of the isolated protein is also useful for conversion of other nitrile compounds to the corresponding amide compounds. Thus, the process for the conversion of a nitrile to an amide comprises: reacting the nitrile with the nitrile hydratase which is produced by Bacillus sp. BR449 deposited as ATCC 202119 which is active at 20° C. to 70° C.; and optionally isolating the amide. The amide is usually not isolated. A distinguishing, novel and useful characteristic of the present invention is that the nitrile hydratase operates at higher temperatures than other nitrile hydratases in the prior art at neutral pH's.

Finally, the present invention relates to an isolated DNA having a nucleotide sequence substantially as shown in SEQ ID NO:6 encoding the amidase gene from BR449 wherein an amidase is produced having the amino acid sequence substantially as shown in SEQ ID NO:7, and an isolated DNA having a nucleotide sequence substantially as shown in SEQ ID NO:12 encoding a protein having an amino acid sequence substantially as shown in SEQ ID NO:13.

It is appropriate to recite the following embodiments for the present invention. The present invention specifically relates to the following isolated DNA embodiments. An isolated DNA encoding a nitrile hydratase consisting of an alpha and a beta subunit wherein the hydratase is optimally active at 55° C., stable at 60° C., and cobalt-containing which is useful for conversion of a nitrile to its corresponding amide without producing significant amounts of its corresponding acid. An isolated DNA wherein the nitrile hydratase has a DNA sequence as set forth in SEQ ID NO:5 wherein the sequence between positions 2312 to 2962 encodes the alpha subunit and the sequence between positions 1606 and 2292 encodes the beta subunit. An isolated DNA encoding a nitrile hydratase wherein the DNA has a nucleotide sequence which has at least 80% identity to the nucleotide sequence between positions 1601 and 2962 as set forth in SEQ ID NO:5. An isolated DNA encoding an alpha subunit of a nitrile hydratase wherein the DNA has a nucleotide sequence which has at least 80% sequence identity to the nucleotide sequence set forth in SEQ ID NO:8 and an isolated DNA encoding a beta subunit of a nitrile hydratase wherein the DNA has a nucleotide sequence which has at least 80% sequence identity to the nucleotide sequence set forth in SEQ ID NO:10. An isolated DNA encoding an amidase wherein the DNA has a nucleotide sequence which has at least 90% sequence identity to the nucleotide sequence set forth between positions 432 and 1475 in SEQ ID NO:5.

The present invention relates to the following thermophilic bacteria embodiments. A thermophilic Bacillus sp. having a nitrile hydratase activity that is activated by a cobalt ion which is useful for conversion of a nitrile to an amide without producing significant amounts of an acid. The thermophilic bacterial strain deposited as ATCC 202119. The thermophilic bacterial strain wherein the nitrile is acrylonitrile, the amide is acrylamide and the acid is acrylic acid.

The bacterial embodiments also include a thermophilic Bacillus sp. having a nitrile hydratase enzyme that is constitutively expressed, optimally active at 55° C., stable at 60° C., and cobalt-containing which is useful for conversion of a nitrile to its corresponding amide without producing significant amounts of its corresponding acid. The Bacillus sp. wherein the nitrile is acrylonitrile, the amide is acrylamide, and the acid is acrylic acid. The Bacillus sp. wherein the Bacillus sp. is deposited as ATCC 202119. The thermophilic Bacillus sp. deposited as ATCC 202119 encodes an amidase activity.

The present invention relates to the following embodiments of processes for converting a nitrile to an amide. A process for conversion of a nitrile to an amide which comprises:(a) reacting the nitrile with a nitrile hydratase which is constitutively produced by a thermophilic Bacillus sp. wherein the nitrile hydratase is active at a temperature between 20° C. to 70° C. and active in the presence of a cobalt ion; and (b) isolating the amide. The process wherein the nitrile is acrylonitrile and the amide is acrylamide. The process wherein the reaction is conducted at a temperature within the range of 20° C. to 70° C. The process wherein the nitrile hydratase is produced by the thermophilic bacterium and wherein the bacterium is deposited as ATCC 202119.

A second process embodiment, is a process for conversion of a nitrile to an amide by the action of a microorganism, the improvement comprises: (a) reacting the nitrile with a nitrile hydratase which is produced by a thermophilic Bacillus sp. which has been cultured in the presence of cobalt ion contained in a culture medium in an amount of about 5 to 20 mg/l and at a temperature of 60° C., to produce the nitrile hydratase in the Bacillus sp. which is active at 20° C. to 70° C.; and (b) isolating the amide produced. The process wherein the nitrile is acrylonitrile and the amide is acrylamide. The process wherein the reaction is conducted at a temperature between 20° C. and 70° C. The process wherein the Bacillus sp. is deposited as ATCC 202119.

A third process embodiment, a process for conversion of a nitrile to an amide which comprises: (a) cultivating a thermophilic Bacillus sp. which has a nitrile hydratase activity that is active within the temperature range of 20° C. to 70° C. in a medium containing a cobalt ion; (b) making a suspension of the thermophilic Bacillus sp.; (c) reacting the nitrile with the suspension of thermophilic bacteria; and (b) isolating the amide. The process wherein the nitrile is acrylonitrile and the amide is acrylamide. The process wherein the reaction is conducted within a temperature range of 20° C. and 70° C. The process wherein the nitrile hydratase is produced by the Bacillus sp. deposited as ATCC 202119.

The present invention also relates to an embodiment which is a process for conversion of a amide to an acid by the action of a microorganism, the improvement comprises: (a) reacting the amide with an amidase which is produced by a thermophilic Bacillus sp. deposited as ATCC 202119 which has been cultured to produce the amidase; and (b) isolating the acid produced. The process wherein the amide is acrylamide and the acid is acrylic acid. The process wherein the Bacillus sp. is deposited as ATCC 202119.

The present invention also embodies a nitrile hydratase produced by a bacteria strain deposited as ATCC 202119. An enzyme having nitrile hydratase activity comprising an alpha subunit which has an amino acid sequence with at least a 90% sequence identity to the sequence in SEQ ID NO:9 and a beta subunit which has an amino acid sequence with at least a 90% sequence identity to the sequence in SEQ ID NO:11.

The present invention embodies a recombinant organism comprising an isolated DNA from a bacterium deposited as ATCC 202119 wherein the DNA encodes alpha and beta subunits of a nitrile hydratase. A recombinant organism comprising an isolated DNA from a bacterium deposited as ATCC 202119 wherein the DNA encodes an amidase having 90% identity to the amino acid sequence as set forth in SEQ ID NO:7.

The present invention is not to be limited to the aforementioned embodiments.

The nitrile hydratase of the present invention is from a thermophilic Bacillus sp. which provides an enzyme catalyst with improved resistance to acrylonitrile inactivation. The improved resistance to inactivation allows the use of increased temperatures for production of acrylamide. The advantages of reactions held at higher temperatures include increased reaction rates, higher solubility of the acrylamide product, and decreased cooling costs for this exothermic reaction. The isolation and properties of a preferred moderately thermophilic Bacillus sp. isolate which produces a thermostable nitrile hydratase is described.

Thermostable nitrile hydratases from aerobic moderate thermophiles were screened for ability to convert acrylonitrile to acrylamide at elevated temperatures and at acrylonitrile concentrations greater than 1%. A new Bacillus sp. (BR449) was discovered which constitutively expresses a thermostable nitrile hydratase having among its properties low substrate inhibition and optimal activity at 55° C. The nitrile hydratase cannot be induced to higher levels by exposing the cells to a nitrile, thus the nitrile hydratase expression is constitutive. The constitutive and non-inducible property of the BR449 nitrile hydratase was an unexpected property of the enzyme which was surprising in view of the prior art which discloses nitrile hydratase enzymes which are inducible. Following prolonged exposure to acrylonitrile, the BR449 nitrile hydratase exhibited a temperature-dependent inactivation by the acrylonitrile, which is attributed to alkylation of the nucleophilic sites on the enzyme.

Bacillus sp. BR449 was deposited with the American Type Culture Collection, 10801 University Boulevard, Manassas, Va. 20110-2209 on Apr. 30, 1998 under the Budapest Treaty as ATCC 202119. All rights to access to the deposited strain are removed upon granting a patent on this invention. It is understood that the process of the present invention is not limited to the deposited BR449 since variants of the strain, i.e., mutants, cell fusion strains or recombinant bacteria strains derived from BR449, can also be used in the process of the instant invention. Examples of such mutants are mutant bacteria that do not express the amidase gene at all and mutants that express the amidase gene but not the genes encoding the nitrile hydratase activity. These mutants can be related bacteria isolates that have either arisen spontaneously or under selection conditions designed to isolate the mutants. Alternatively, recombinant bacteria which selectively express either the amidase gene or the nitrile hydratase genes can constructed using any of the genetic engineering methods that are well known to those skilled in the art. Mutant or recombinant bacteria having no residual amidase activity will convert all of a nitrile substrate to its amide without production of any of the corresponding acid as a by-product. Conversely, mutant or recombinant bacteria that express the amidase gene to the exclusion of the nitrile hydratase gene are useful for converting amides to the corresponding acids.

In practicing the process of the present invention, BR449 is cultured for 2 to 3 days in culture medium containing a carbon source such as glucose. An example of a suitable medium is OP medium which is set forth in Example 1. During cultivation, it is preferable to include at least one divalent metal salt at a concentration of approximately 20 mg/l in the growth medium. The preferred divalent metal salt is $Co^{2+}$. After cultivation, the cells are collected from the culture medium by centrifugation and the pelleted cells resuspended in a buffer (e.g., potassium phosphate buffer) containing acrylonitrile.

The nitrile hydratase reaction is conducted in an aqueous suspension containing about 1 to 20 mg (dry weight) cells/ ml and acrylonitrile between 1% and 5% by weight, preferably around 1%, in a potassium phosphate buffer at a pH between 6 and 9, preferably around 7.5. The reaction temperature is between 20° C. and 70° C. with the preferred temperature at 22° C. which maximizes the yield of acrylamide from acrylonitrile by prolonging the lifetime of the catalyst. However, at a temperature of 55° C. the nitrile hydratase activity is at a maximum but with a shorter half-life because of alkylation by of the nucleophilic sites on the enzyme. Therefore, the choice as to whether the reaction is conducted at 22° C. or 55° C., or at a temperature in between, will depend on which is more important to the practitioner, nitrile hydratase reaction speed or longevity. Additionally, during the reaction, the concentration of acrylonitrile can be maintained at a preferred concentration by subsequently adding acrylonitrile to the reaction to replace the acrylonitrile that has been converted to acrylamide. The reaction is allowed to proceed for approximately two hours and the acrylamide formed during the reaction is recovered by art-known methods.

For example, the BR449 cells can be separated from the reaction mixture by centrifugation, followed by treatment with activated charcoal or an ion exchange resin to remove contaminants. Then, the amide compound can be concentrated or precipitated by distillation or evaporation under reduced pressure. Though further purification of the amide is usually not performed, the precipitated amide crystals can be recrystallized from an organic solvent such as chloroform or methanol to give the purified amide compound.

While the present invention can be practiced with intact cells, it can, from the standpoint of repeated use, continuous operation and product recovery, be preferable to immobilize the cells. Any method of immobilizing cells which is known in the art and which does not substantially reduce the nitrile hydratase activity can be used. Preferred methods include immobilization in agarose, alginate, and polyacrylamide. Examples of techniques for cell immobilization and use of immobilized cells in manufacture of amides have been described in U.S. Pat. No. 4,248,968 to Watanabe et al which is herein incorporated by reference.

Cell immobilization can be accomplished by suspending the BR449 cells in a suitable aqueous medium such as physiological saline or buffered solution containing an acrylamide monomer and cross-linking agent, then adding a suitable polymerization initiator and polymerization accelerator to the suspension and allowing the polymerization to proceed.

The acrylamide monomers used to immobilize the BR449 cells include, for example, acrylamide, methacrylamide, etc. The concentration of each monomer in the reaction should be sufficient to form a gel as a result of the polymerization reaction, and is usually between 2 and 30% by weight, based on the reaction solution. The cross-linking agents include N,N'-methylenebisacrylamide, 1,3-di-(acrylaminomethyl)-2-imidazolidone, etc. Ammonium persulfate or potassium persulfate are examples of polymerization initiators suitable for the reaction. Dimethylaminopropionitrile and triethanolamine are examples of polymerization accelerators suitable for the reaction. Any polymerization initiator or accelerator which minimally inhibits the activity of microorganisms is suitable.

Thus, there can be obtained polymer gels containing the BR449 cells which are immobilized. The gel so obtained can be crushed and used in batch method to convert acrylonitrile to acrylamide. Alternatively, the crushed gel can be packed into a column and acrylonitrile bearing solution is pumped through the column wherein the acrylonitrile is converted to acrylamide. The immobilized cells as described above can be used in a continuous column procedure.

The continuous column method uses one or a plurality of columns connected to each other in series, which are filled with the immobilized BR449 cells. The immobilized cells are crushed to a size within the range of 0.5 to 5 mm and packed into the columns at a density between 0.3 to 0.5 g immobilized cells/cc. Then, the nitrile such as acrylonitrile is continuously fed into the column as an aqueous solution via the column inlet and, at the same time, continuously feeding the nitrile at an intermediate stage or location before completion of the reaction in an amount soluble in the reaction solution. In situations where one column is needed or used, a sectional column having one or more feed inlets provided between the column inlet and column outlet, and which comprises a few sections is preferable.

In addition to columns consisting of immobilized cells or batches containing free or immobilized cells, batches or columns containing crude or purified nitrile hydratase enzyme preparations can also be used. The advantage over using cells, either whole or immobilized, is that a much higher specific activity per unit volume or area can be achieved using enzyme extracts as opposed to intact cells. The cost of isolating BR449 nitrile hydratase can be made extremely cost effective by cloning the nitrile hydratase genes in an organism such as *E. coli* using high copy number or high expression plasmid vectors to produce the nitrile hydratase. In this manner, quantities of nitrile hydratase can be produced that are much higher than the quantities that are obtainable using BR449 cells to isolate the nitrile hydratase enzyme.

As mentioned above, the isolated DNA encoding nitrile hydratase can be isolated from BR449 and the genes encoding the alpha and beta subunits cloned into a suitable organism. The advantages for cloning the nitrile hydratase gene of BR449 into another organism are many-fold. The first advantage is that organism contains many copies of the gene which enables each organism to produce more of the enzyme compared to the quantities produced by BR449 cells. This is useful both using the whole cell method for converting a nitrile to its corresponding amide and when the enzyme is to be purified. A second advantage is that the expression of the enzyme can be made to be inducible when the genes are operably linked to an inducible promoter. In BR449, the nitrile hydratase is continuously expressed and is not inducible. It can be anticipated that for certain applications it can be advantageous to operably link the nitrile hydratase genes to promoters that are inducible. Such promoters can be used to limit expression to those times when expression is needed. A third advantage is that the nitrile hydratase reaction can be performed at lower temperatures which prolongs the half-life of the enzyme and is useful for some conversions. Thus, at the lower temperature, more of the amide product is produced per reaction. A novel characteristic of the enzyme is its ability to operate at higher temperatures than similar nitrile hydratases in the prior art at neutral pH's. A fourth advantage is that the nitrile hydratase can be expressed in non-procaryote organisms such as yeast or plants. In plants the nitrile hydratase expression can be directed to specific parts of the plant such as the seeds or fruiting bodies which can be a very effective means for producing the nitrile hydratase. Examples of plants that are useful for expressing the nitrile hydratase or amidase genes are crop plants such as corn or tobacco, aquatic plants such as algae, or weedy plants like *Arabidopsis thaliana*.

The molecular biology techniques that can be used to clone the BR449 nitrile hydratase genes are well-known in the art (Sambrook et al., *Molecular Cloning: A Laboratory Manual*, Cold Spring Harbor Laboratory, Cold Spring Harbor, N.Y. (1989) is an example of an authoritative guide to molecular biology) and expression vectors suitable for expression of the genes in procaryote and/or eukaryote cells are commercially available from a large number of vendors. Transformation and transfection techniques such as cell fusion, electroporation, biolistic or conventional injection are also well-known in the art and are described in Sambrook et al (ibid.). Other methods which are common specifically to plants include Agrobacterium-mediated transformation and biolistic injection.

An attractive and useful purpose for expressing the nitrile hydratase genes in another organism is that the expression of the alpha and beta subunits can be uncoupled from expression of the amidase gene. Thus, recombinant organisms can be made which do not express any amidase activity at all, unlike the in BR449. Conversely, recombinant organisms can also be made which express only the amidase activity without any nitrile hydratase activity. These recombinant organisms can be used to convert amides to the corresponding acid. Also, by operably linking the nitrile hydratase gene or the amidase gene to the appropriate promoter expression of the gene in the recombinant organism can be increased many-fold over expression in BR449, or made inducible so that expression of the two genes can be differentially regulated.

The following examples are intended to promote a further understanding of the present invention.

EXAMPLE 1

This example shows the isolation and characterization of nitrile-degrading thermophilic bacteria. In particular, the BR449 isolate is described and the properties of its nitrile hydratase is provided.

MATERIALS AND METHODS
Isolation of Acrylonitrile-degrading Thermophiles

Nitrile-degrading thermophilic bacteria were isolated from acrylonitrile enrichments of soil samples collected from pristine and polluted locations in Michigan and incubated at 60° C. The enrichment medium (DP) was designed to provide nutrients for more fastidious organisms, but to select for organisms capable of growth using acrylonitrile as a principal carbon source. The OP medium at pH 7.2 contained per liter: $K_2HPO_4$, 0.5 g; NH Cl, 1 g; MgSQ, 20 mg; yeast extract, 0.2 g; casamino acids, 0.1 g; trace element solution, 1 ml (Barnett, J. A., et al., J. Appl.

Bacteriol. 18: 131–145 (1955)), and acrylonitrile, 2 g. Primary isolations were obtained by spreading week-old suspensions of enrichment cultures on DP plates containing 0.2% acrylonitrile followed by incubation at 60° C. in sealed plates. Re-streaking of isolates at progressively higher acrylonitrile concentrations yielded thermophiles capable of growth on acrylonitrile at concentrations up to 1%.

Growth of Bacillus Isolates

Bacillus sp. BR449 (ATCC 202119) was grown in OP medium at pH 7.2 which contained per liter: $KH_2PO_4$, 1 g; $K_2HPO_4$, 0.5 g; yeast extract, 1 g; malt extract, 1 g; peptone 2 g; glycerol, 3 g; casamino acids, 0.1 g. The isolate was grown at 60° C. using turbidity to monitor culture density. Divalent metal salts were added to the growth medium where indicated in concentrations of 20 mg/l.

Nitrile Hydratase and Amidase Assay

Nitrile hydratase activity was measured using whole cells in assays containing 20 mg (dry wt) cells, in 1 ml 0.5 M acrylonitrile and potassium phosphate buffer, containing 0.5 M acrylonitrile, pH 7.5. The reaction mixture was incubated in a water bath at 50° C. with shaking for 10 minutes, and the reaction stopped by addition of 0.2 ml 2 N HCl. Acrylamide formation was measured using HPLC by injection into a Novapak C-18 reverse phase column and eluted with 1:12 acetonitrile:5mM potassium phosphate buffer, pH 2.5. Peaks were identified at 200 nm with a Waters (Newton, Mass.) variable wavelength detector and analyzed with reference to chemical standards. One unit of nitrile hydratase-activity is defined as the formation of one $\mu$mole acrylamide per minute. Amidase activity was measured in the same manner using 0.5 M acrylamide as substrate by measurement of acrylic acid formation.

Enzyme Stability Studies

For studies of nitrile hydratase stability, whole cells of BR449 were incubated at varied temperatures in 50 mM potassium phosphate buffer, pH 7.5, following which the nitrile hydratase assay was carried out at 50° C.

Thermophile Identification

Thermophile isolate BR449 was identified by 16S ribosomal gene sequence using universal primers and PCR methods described by Maltseva et al (Maltseva, O., et al., Microbiology 142:1115–1122 (1996)). Amplified DNA product was sequenced at the Michigan State University Sequencing Facility, East Lansing, Michigan using an Applied Biosystems Model 173A automatic sequencer. Partial sequences were compared to Gene Bank data using the Basic Local Alignment Search Tool (BLAST) from the National Center of Biotechnology Information and the Ribosomal Database Project.

RESULTS

Characteristics of Thermophile Isolates

Following acrylonitrile enrichment of soil samples collected from varied locations, 50 isolates were selected for their growth ability on acrylonitrile. Of these, six demonstrated good growth at acrylonitrile concentrations higher than 0.2% at 50–60° C. All six isolates grew well at 50–60° C., with no growth observed at 45° C. While similar in appearance and colony morphology, these isolates demonstrated significant differences in nitrile hydratase and amidase expression.

TABLE 1

Nitrile degrading enzymes in the new isolates

| New Organisms | Nitrile Hydratase Specific Activity (U/mg) | Amidase Specific Activity (U/mg) |
| --- | --- | --- |
| BR443 | 3.0 | 21.4 |
| BR444 | 47.2 | 15.5 |
| BR445 | 19.2 | 17.5 |
| BR446 | 24.8 | 4.9 |
| BR447 | 1.1 | 7.0 |
| BR448 | 0.8 | 14.6 |
| BR449 | 77.6 | 11.3 |

Of these, isolate BR449 demonstrated the highest nitrile hydratase activity with only modest amidase activity, and was selected for detailed study (Table 1). This isolate could readily grow on plates and in liquid culture in 1% acrylonitrile, a concentration toxic to most other bacteria. In addition, the hydratase of BR449 proved to be quite resistant to acrylonitrile substrate inhibition, with only 47% inhibition in the presence of 1oo% acrylonitrile during assay at 50° C. (FIG. 1).

Identification of BR449

The genus/species of BR449 was determined by comparing its 16S ribosomal (rRNA) gene sequence to the 16S rRNA gene sequence of other bacteria. PCR using universal primers and PCR methods described by Maltseva et al., Microbiology 142: 1115–1122 (1996) was used to isolate a 1.4 kb PCR product which encoded residues of the BR449 16S rRNA gene. The 1.4 kb PCR product was sequenced at the Michigan State University Sequencing Facility using an Applied Biosystems Model 173A automatic sequencer and partial DNA sequences were analyzed using the Basic Local Alignment Search Tool (BLAST) from the National Center of Biotechnology Information (NCBI) and the Ribosomal Database Project.

The sequences producing significant alignments are shown in Table 2.

TABLE 2

Sequences producing significant alignments

| Identification No. | Description | (Bits) | Value |
| --- | --- | --- | --- |
| emb\|Z26929\|BS16SRRNA | Bacillus sp. gene for 16S ribosomal RNA | 997 | 0.0 |
| emb\|Z26930\|BP16SRRNA | B. pallidus gene for 16S ribosomal RNA | 975 | 0.0 |
| emb\|Z26931\|BT16SRRNC | B.thermoalkalophilus gene for 16S ribosoma . . . | 888 | 0.0 |
| gb\|U59630\|BSU59630 | Bacillus ICPS6 16S ribosomal RNA gene, seque . . . | 720 | 0.0 |
| gb\|LO9227\|SANRDGX | Saccharococcus thermophilus 16S ribosomal RNA . . . | 718 | 0.0 |
| gb\|L29507\|BAC1RRAAA | Bacillus sp. 16S ribsomal RNA (16S rRNA) gene. | 714 | 0.0 |
| gb\|AF067651\|AF067651 | Bacillus caldoxylolyticus 16S ribosomal RN . . . | 702 | 0.0 |
| emb\|Z26926\|BT16SRRNG | B.thermocatenulatus gene for 16S ribosomal . . . | 678 | 0.0 |
| emb\|X62178\|BANCIMB | B.aminovorans NCIMB 8292 (T) rRNA | 672 | 0.0 |
| emb\|Z26922\|BC16SRRNB | B.caldotenax gene for 16S ribosomal RNA | 668 | 0.0 |
| gb\|M77485\|BACRRSSB | Baciilus caldoveiox (DSM 411) ribosomal RNA . . . | 668 | 0.0 |
| emb\|Z26923\|BT16SRRNB | B.thermoleovorans gene for 16S ribosomal RNA | 664 | 0.0 |
| gb\|M77484\|BACRRSSA | Baciilus caidolyticus (DSM 405) ribosomal RN . . . | 664 | 0.0 |
| emb\|Z26924\|BC16SRRNC | B.caldoiyticus gene for 16S ribosomal RNA | 662 | 0.0 |
| emb\|X60618\|BKAU16SR | B.kaustophilus 16S ribosomal RNA | 656 | 0.0 |
| emb\|Z26927\|BD16SRRNB | B.denitrificans gene for 16S ribosomal RNA | 656 | 0.0 |
| emb\|Z26928\|BT16SRRNH | B.thermodenitrificans gene for 16S ribosom . . . | 654 | 0.0 |
| gb\|N77487\|BACRRSSD | Bacilius thermodenitrificans (NCIMB 11730) r . . . | 652 | 0.0 |
| gb\|M77488\|BACRRSSE | Bacillus thermoleovorans (ATCC 43513) riboso . . . | 644 | 0.0 |
| emb\|Z26925\|BC16SRRND | B.caidovelox gene for 16S ribosomal RNA | 636 | 0.0 |
| emb\|X60641\|BTHER16SR | B.thermoglucosadicus 16S ribosomal RNA | 636 | 0.0 |
| emb\|AJ011362\|UBA011362 | uncultured bacterium 16S rRNA gene, part . . . | 630 | e-179 |
| emb\|X57309\|BS16SRNA | B.stearothermophilus 16S rRNA | 628 | e-178 |
| emb\|XE2180\|BCDSMRRNA | B.caldotenax DSM 406(T) rRNA | 618 | e-175 |
| gb\|AF078814\|AF078814 | Bacillus sp. 4830 16S ribosomal RNA gene, . . . | 593 | e-167 |
| gb\|AF001964\|BFAF001964 | Bacillus. flavothermus isolate AB095 16S . . . | 581 | e-164 |
| gb\|AF001961\|BFAF001961 | Bacillus flavothermus isolate AB002 16S . . . | 581 | e-164 |
| emb\|Z26932\|BF16SRRNA | B.flavothermus gene for 16S ribosomal RNA | 549 | e-154 |
| gb\|AF001963\|BFAF001963 | Bacillus flavothermus isolate AB004 16S . . . | 543 | e-152 |
| emb\|Z26935\|BS16SRRNC | B.smithii gene for 16S ribosomal RNA | 541 | e-152 |

TABLE 2-continued

Sequences producing significant alignments

| Identification No. | Description | (Bits) | Value |
|---|---|---|---|
| gb\|AF001962\|BFAF001962 | *Bacillus flavothermus* isolate AB003 16S . . . | 537 | e-151 |
| gb\|U46747\|B0U46747 | *Bacillus sp.* OS-ac-18 16S ribosomal RNA gene . . . | 533 | e-149 |
| emb\|X6446S\|BM16SRRN | *B.methanolicus* 16S ribosomal RNA | 509 | e-142 |
| eeb\|X60643\|B8M1168R | *D.smithii* 16S ribosomal RNA | 507 | e-142 |
| emb\|Z99104\|BSUB0001 | *Bacillus subtilis* complete genome (section . . . | 494 | e-138 |
| dbj\|D2618S\|BAC180K | *B.subtilis* DNA, 180 kilobase region of repl . . . | 494 | e-138 |
| dbj\|AB020193\|AB020193 | *Bacillus sp.* DNA for 16S ribosomal RNA, s . . . | 494 | e-138 |
| gb\|K00637\|BACRGRRNB | *B.subtilis* rrnB operon with 23S rRNA, 16SrR . . . | 494 | e-138 |
| emb\|X94558\|HL\|6SRRN1 | *H.litoraiis* 16S rRNA gene | 494 | e-138 |

The BR449 16S rRNA gene sequence (SEQ ID NO:1) shown in FIG. 6 showed 100% identity to the 16S rRNA gene sequence of Bacillus sp13 (SEQ ID NO:2) as shown in FIG. 7. When the 16S RNA gene sequence from BR449 was compared to the 16S rRNA gene sequence of Bacillus pallidus (SEQ ID NO:3), an identity of 99.6% was shown (FIG. 8). Finally, the 16S RNA gene sequence from BR449 was compared to the 16S rRNA gene sequence of *Bacillus smithii* (SEQ ID NO:3). As shown in FIG. 9 BR449 showed an identity of only 91.7%.

These results indicate that BR449 is not closely related to *Bacillus smithii*, but is a Bacillus strain which is very closely related to *Bacillus pallidus*, and virtually indistinguishable from Bacillus sp13 based on 16S RNA comparisons. The 100% identity of BR449 to Bacillus sp. is based on 16S RNA comparisons and there may be other genomic sequences which would show that BR449 is also distinct from Bacillus sp13. Although Bacillus sp13 has not been validly described, it is differentiated from other members of the moderate thermophile group by lack of extracellular amidase activity (Rainey, F. A., et al., FEMS Microbiol. Lett. 115: 205–212 (1994)). BR449 also does not show extracellular amidase activity, which is consistent with the 16S rRNA gene sequence comparisons and further indicates that BR449 is more related to Bacillus sp13 and *Bacillus pallidus* than to *B. smithii*.

Effect of Additions on Nitrile Hydratase Activity

Divalent metal ions were added during growth of isolate BR449 to provide indications of metals stimulatory to nitrile hydratase production. As shown in Table 3, addition of divalent cobalt greatly increased the specific activity of nitrile hydratase expressed by the cells.

TABLE 3

Effect of metal ions on nitrile hydratase activity

| Metal Ions | Total Cells (mt/l, dry weight) | Nitrile hydratase Specific Activity (U/mg) | Amidase Specific Activity (U/mg) |
|---|---|---|---|
| None | 90 | 3.2 | 1.8 |
| $Co^{2+}$ | 225 | 71.5 | 9.7 |
| $Cu^{2+}$ | 90 | 1.9 | 1.5 |
| $Fe^{2+}$ | 490 | 4.3 | 2.3 |
| $Mn^{2+}$ | 65 | 2.2 | 2.1 |
| $Ni^{2+}$ | 80 | 6.8 | 3.4 |

This finding indicates that the BR449 nitrile hydratase is a cobalt-containing enzyme family which includes the *Rhodococcus rhodochrous* J1 and *Pseudomonas putida* NRRL-18668 nitrile hydratases (Nagasawa, T., et al., Appl. Microbiol. Biotechnol. 40:189–195 (1993); and Payne, M. S., et al., Biochemistry 36:5447–5454 (1997)). Induction of hydratase activity by addition of acrylonitrile during BR449 growth was without effect indicating constitutive enzyme production by the isolate. No organic acids were necessary to preserve enzyme stability.

Temperature and pH Optimum of BR449

Figure 2:
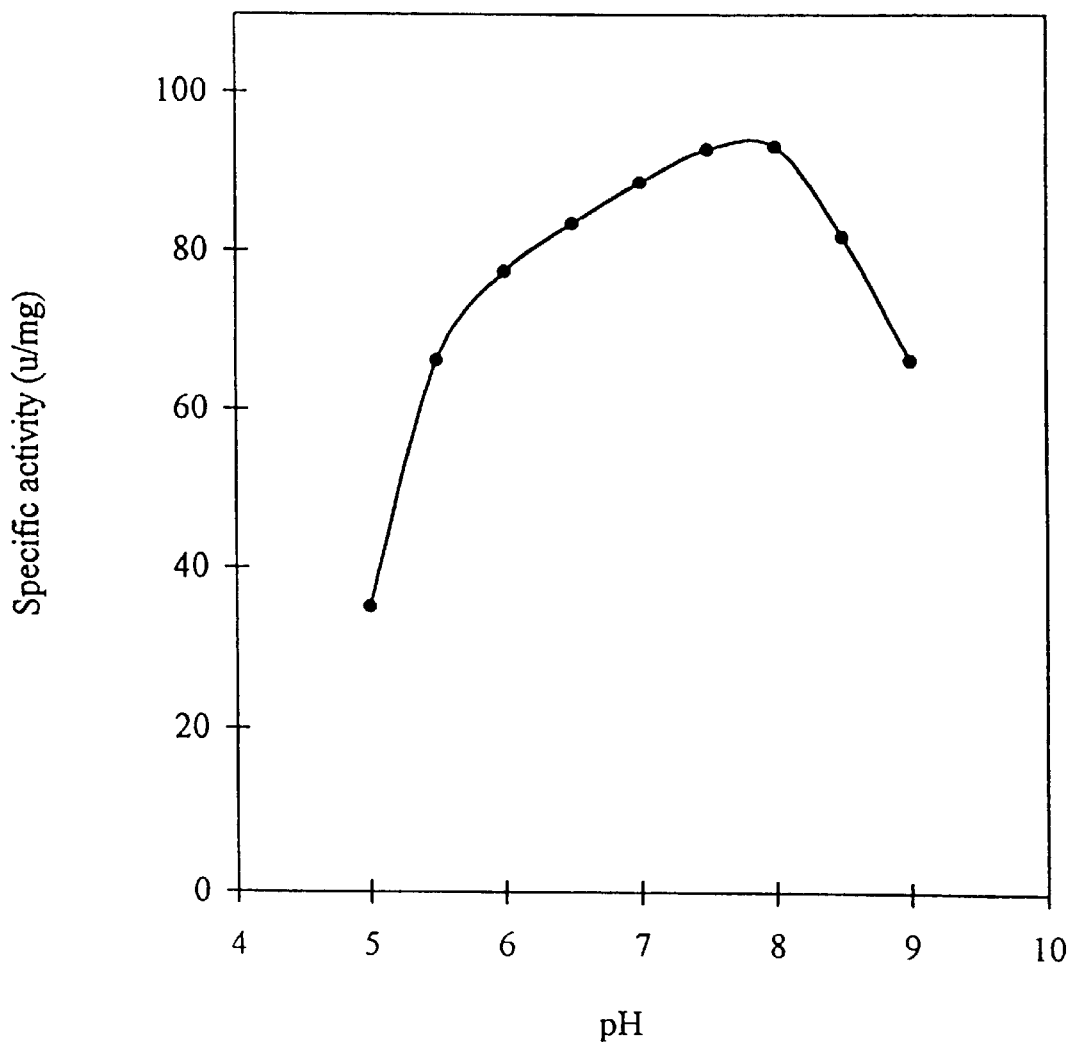
FIG. 2 is a graph showing pH dependence of BR449 nitrile hydratase assayed at 50° C.
Figure 3:
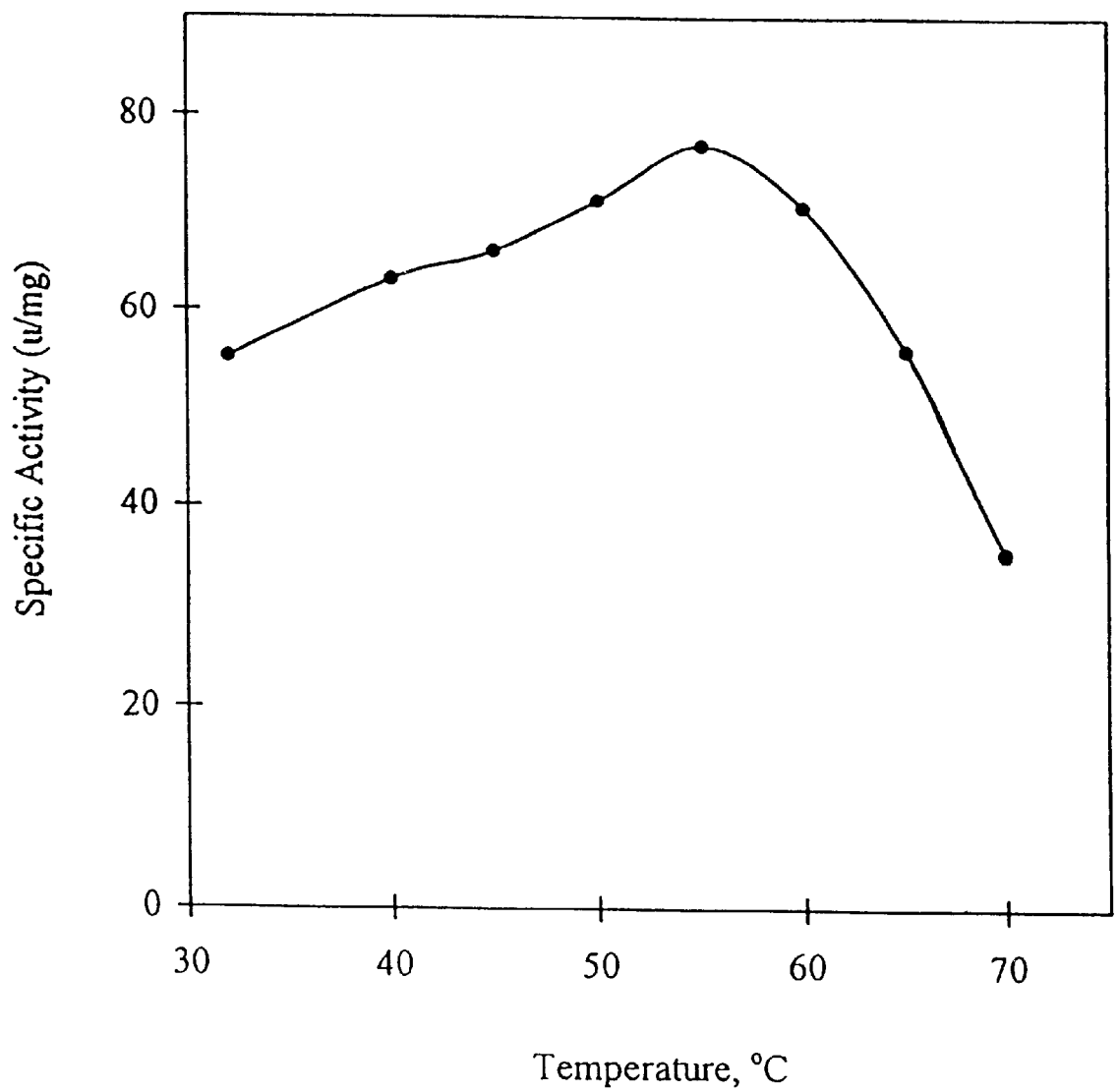
FIG. 3 is a graph showing nitrile hydratase activity as a function of temperature.
Figure 4:
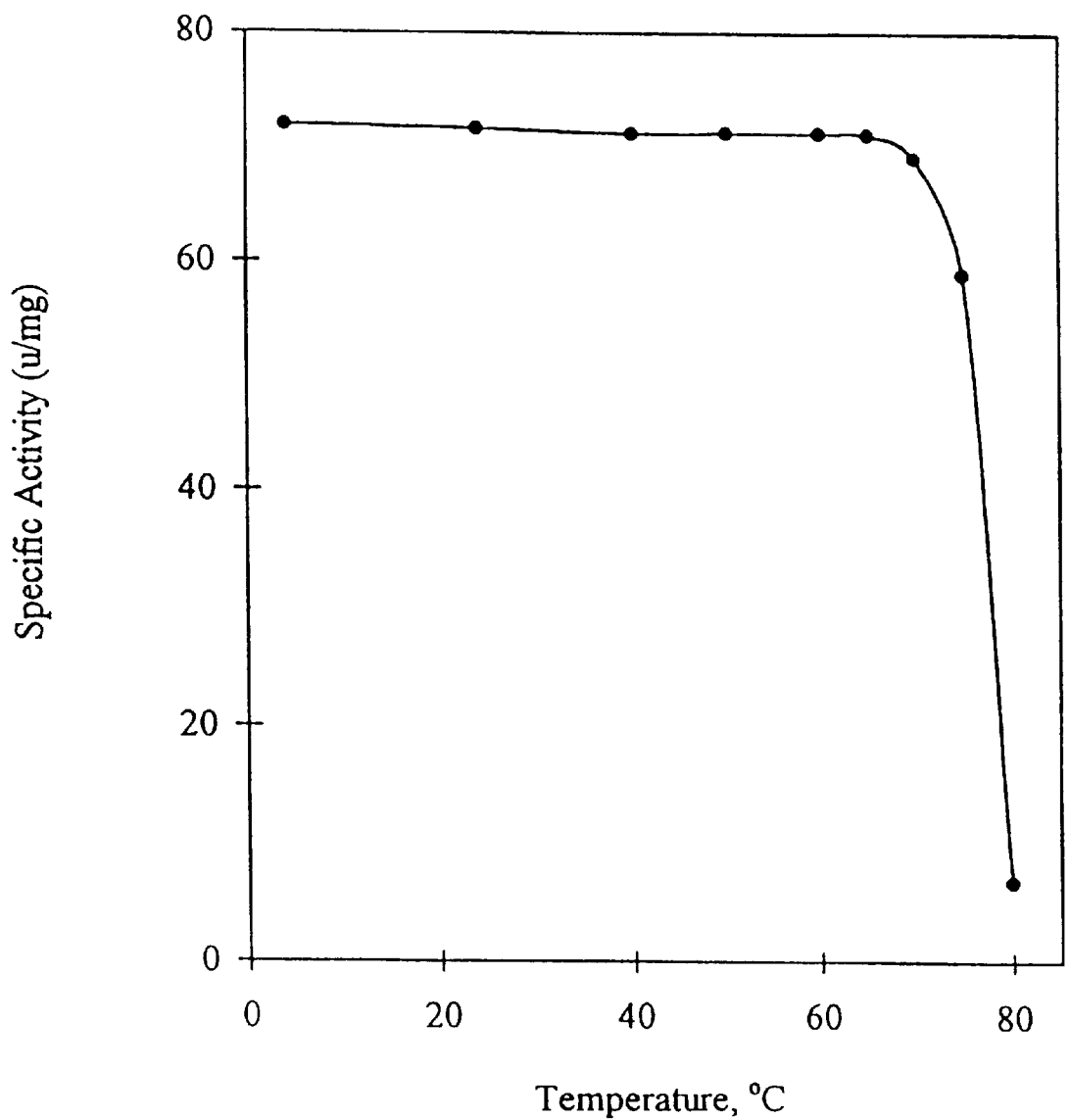
FIG. 4 is a graph showing nitrile hydratase stability. Closed circles designate specific activity in the standard assay at 50° C. after two hours incubation at the temperature indicated.

BR449 showed a broad pH optimum for activity, with a maximum near pH 7.5 (FIG. 2). The BR449 nitrile hydratase has a surprisingly broad temperature range between 20° C. and 70° C., with an optimum at 55° C. In separate enzyme stability studies, the BR449 nitrile hydratase proved stable during two hour incubations in buffer at temperatures to 60° C., with inactivation ensuing above this temperature (FIGS. 3 and 4).

Acrylamide Production

Figure 5:
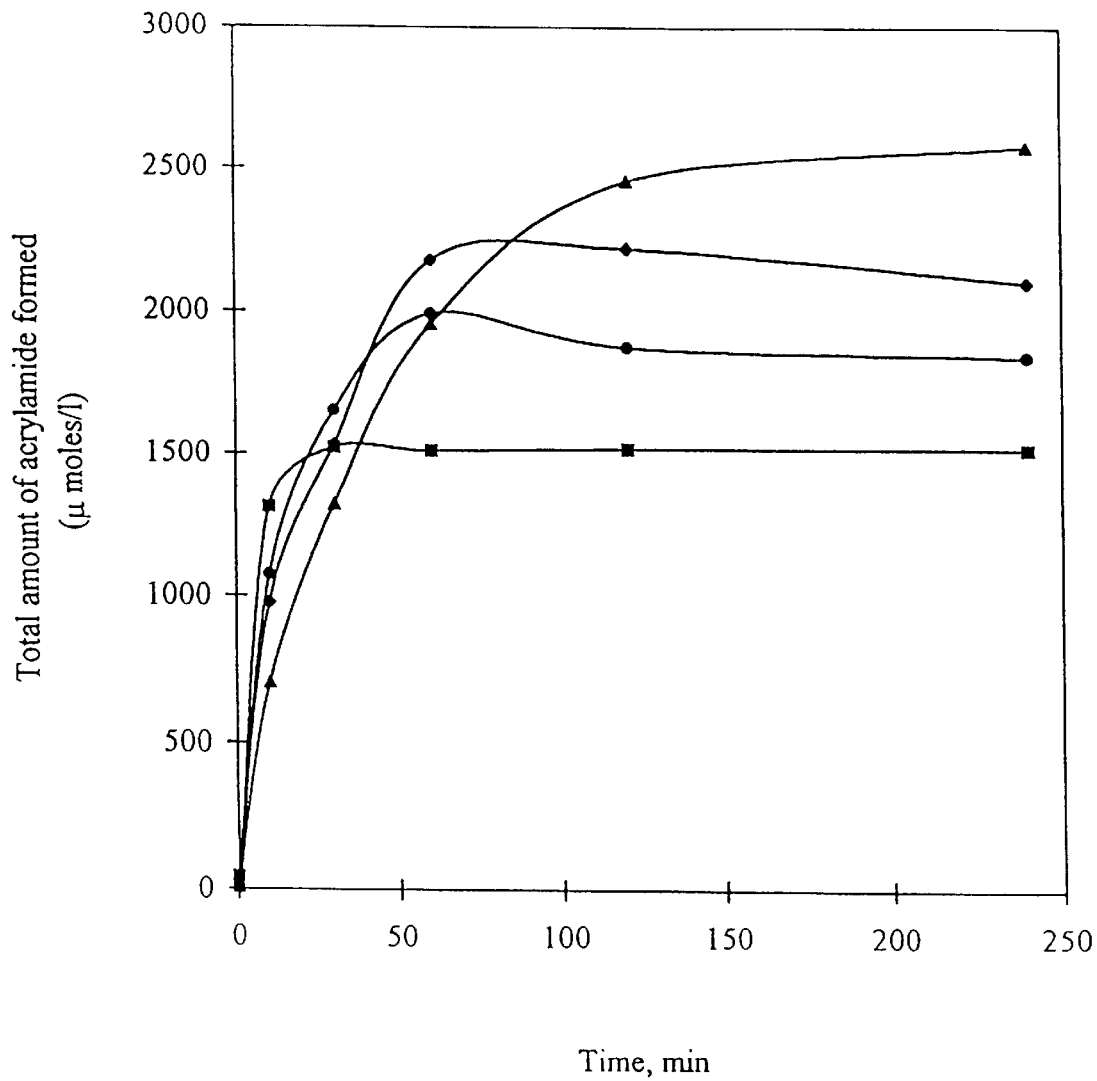
FIG. 5 is a graph showing acrylamide production using whole BR449 cells in 2% acrylonitrile. The temperatures are: ■ 50° C., ● 40° C., ♦ 30° C., and Δ 22° C.

In preliminary experiments to determine rates of acrylamide production with temperature, 20 mg dry weight BR449 cells were incubated with shaking in 2% acrylonitrile, 50 mM phosphate buffer, pH 7.5. As seen in FIG. 5, initial reaction rates at higher temperatures were initially rapid, but ceased after one hour or less. This proved to be due to catalyst inactivation, as dilution with fresh substrate was without effect (data not shown). Although the initial reaction was slower, lowering the reaction temperature to 22° C. resulted in prolonged catalyst lifetime and increased product formation.

DISCUSSION

Aerobic thermophiles were isolated which are able to grow in acrylonitrile concentrations of 1%. Bacillus sp. BR449 proved of particular interest in its tolerance to acrylonitrile, as well as high nitrile hydratase activity. Stimulation of enzyme specific activity in this isolate with cobalt addition to the growth medium suggests that the BR449 nitrile hydratase is likely to be a member of the cobalt-containing family. While the BR449 hydratase resists inhibition by concentrated acrylonitrile in shorter term assay at 50 degrees, longer term incubations in 2% acrylonitrile resulted in highly temperature-dependent inactivation, even at temperatures where the enzyme was stable in buffer. Since the propensity for vinyl compounds including acrylonitrile to alkylate the nucleophilic protein residues histidine and cysteine is well established (Friedman, M., J. Am. Chem. Soc. 87:3672–3682 (1967)), inactivation was likely due to acrylonitrile alkylation of nucleophilic enzyme residues important for conformational stability and/or catalytic activity, and at enzyme locations vulnerable to attack such as the active site.

Although the determinants of enzyme stability are becoming increasingly understood (Dill, K. A., Biochemistry 29:7133–7157 (1990)), the relationships between enzyme thermostability and resistance to chemical inactivation have been less well investigated. It is generally recognized that at the same temperature, thermostable enzymes have less flexibility than their thermolabile counterparts, and are therefore more resistant to chemical denaturants (Tombs, M. P., J. Appl. Biochem. 7:3–24 (1985)). Studies of spontaneous deamination, a major source of enzyme inactivation at both moderate and high temperatures, have demonstrated the important influences of conformational stability and neighboring residues on rates of inactivation (reviewed in Daniel, R. M., Enz. Microb. Technol. 19:74–79 (1996)).

Thus, although the nitrile hydratase of Bacillus sp. BR449 exhibits a number of attractive scientific and biotechnological attributes, it is likely that identification and site-directed replacement of the alkylation-sensitive residues can provide an even more effective catalyst for acrylonitrile industrial bioconversions at elevated temperatures. The DNA encoding the enzyme can be isolated and inserted in another bacterium such as E. coli for production of the enzyme.

EXAMPLE 2

A 3.3 kb DNA fragment of BR449 was sequenced and identified as containing the coding region for the beta subunit and the coding region for the alpha subunit of the BR449 nitrile hydratase. Also located on the DNA fragment is the gene encoding the amidase gene and an open reading frame 1 designated as ORF1 of unknown activity. The DNA sequence of the 3.3 kb DNA fragment is shown in FIG. 10 (SEQ ID NO:5).

The amino acid sequence of the alpha subunit encoded by SEQ ID NO:8 is shown in FIG. 11. The alpha subunit is a 214 amino acid protein (SEQ ID NO:9). The amino acid sequence of the BR449 alpha subunit was compared to the 220 residue amino acid sequence of the alpha subunit of the nitrile hydratase of Bacillus smithii strain SC-J05-1 disclosed in U.S. Pat. No. 5,563,053 to Takashima (SEQ ID NO:15). FIG. 16 shows that the amino acid sequence of the BR449 alpha subunit had no more than an 87.7% identity to the amino acid sequence of the alpha subunit of Bacillus smithii. When the DNA sequence encoding the BR449 alpha subunit (SEQ ID NO:8) was compared to the DNA encoding the alpha subunit of Bacillus smithii (SEQ ID NO:14), the results showed only an 81.4% degree of identity (FIG. 15). These results show that the gene sequence encoding the alpha subunit of the BR449 nitrile hydratase, while related, is distinct from the homologous gene in Bacillus smithii.

The amino acid sequence of the beta subunit encoded by SEQ ID NO:10 is shown in FIG. 12. The beta subunit is 229 amino acids (SEQ ID NO:11). The beta subunit was compared to the 229 residue amino acid sequence of the beta subunit of the nitrile hydratase of Bacillus smithii strain SC-J05-1 (SEQ ID NO:17). FIG. 18 shows that is no more than 82.5% identity between the amino acid sequences of the beta subunit of BR449 to Bacillus smithii. When the DNA sequence encoding the BR449 beta subunit (SEQ ID NO:10) was compared to the DNA encoding the beta subunit of Bacillus smithii (SEQ ID NO:17), the results showed only an 85.6% degree of identity (FIG. 17). These results show that the gene sequence encoding the beta subunit of the BR449 nitrile hydratase, while related, is distinct from the homologous gene in Bacillus smithii.

The sequence for the amidase gene (SEQ ID NO:6 is shown in FIGS. 13A and 13B.

The amino acid sequence of ORF1 encoded by SEQ ID NO:12 is shown in FIG. 14. ORF1 is 101 amino acids (SEQ ID NO:13) and a homology search shown in FIG. 19 showed that ORF1 has an amino acid sequence that appears to have limited identity (score 77.6) to the amino acid sequence of the beta subunit of Rhodococcus rhodochrous nitrile hydratase (SEQ ID NO:18).

While the nitrile hydratase of BR449 has limited amino acid identity to the nitrile hydratase of Bacillus smithii (87.7% and 85.6% for the alpha and beta subunits respectively), the sequence analysis clearly shows that the nitrile hydratase gene of these two organisms are distinct. Thus, these amino acid sequence differences and the 16S RNA sequence data in Example 1 indicate that BR449 is a new and hitherto unknown species of Bacillus. Accordingly, the biochemical properties of the BR449 nitrile hydratase shown herein is distinct from that of other microorganisms.

EXAMPLE 3

The following Example shows the production of acrylamide from acrylonitrile using intact cells in a batch method. BR449 cells are cultured at 60° C. in DP medium containing 20 mg/l $Co^{2+}$. After 2 to 3 days, the cells are collected from the culture medium by centrifugation.

The pelleted cells are resuspended at a concentration between 1 to 20 mg (dry weight) cells/ml in a potassium phosphate buffer at pH 7.5 containing 2% acrylonitrile. The reaction temperature is at 22° C. which maximizes the yield of acrylamide from acrylonitrile by prolonging the lifetime of the catalyst. During the reaction, the cells are continuously agitated and the concentration of acrylonitrile is maintained at 2% by adding acrylonitrile dropwise to the reaction. After 2 to 2.5 hours or longer, the acrylamide is measured directly from the reaction. Alternatively, the cells can be pelleted and the acrylamide recovered from the supernatant fraction by chloroform extraction.

EXAMPLE 4

An example for the preparation of immobilized BR449 cells for use in batch production of acrylamide from acrylonitrile is as set forth below.

Four parts of intact BR449 cells (water content about 75%) grown in the presence of $Co^{2+}$ as described in Example 4, 0.45 parts of acrylamide, 0.05 parts of N-N'-methylenebisacrylamide, and 4 parts of physiological saline are mixed to prepare a uniform suspension. To this suspension, 0.5 parts of a 5% dimethylaminopropionitrile solution and 1 part of a 2.5% potassium persulfate solution are added. The reaction is maintained at 10° C. to 15° C. for 30 minutes to allow polymerization. After polymerization, the cell-containing gels are crushed and washed with physiological saline to give 10 parts of immobilized cells.

Measurement of acrylamide producing ability of immobilized BR449 cells is compared to intact BR449 cells. 0.8 part of intact cells or 2 parts of the immobilized cells are diluted with 0.05 M phosphate buffer (pH 8.0) to make 100 parts. Then, for each dilution, equal parts of the diluted solution and 2% acrylonitrile are mixed together, and allowed to react at 22° C. to 60° C. for 30 minutes with stirring. Production of acrylamide in each of the reaction mixtures is determined using a Novapak C-18 reverse phase HPLC column as in Example 1.

EXAMPLE 5

An example for the preparation of immobilized BR449 cells for use in column production of acrylamide from acrylonitrile is as set forth below.

Forty parts of intact BR449 cells grown in the presence of $Co^{2+}$ as in Example 4 is mixed with 4.5 parts acrylamide, 0.5 parts N,N'-methylenebisacrylamide and 40 parts physiological saline to prepare a uniform suspension. To this suspension is added 5 parts 5% dimethylaminopropionitrile and 10 parts of a 2.5% potassium persulfate solution. The mixture is allowed to polymerize at 10° C. for 30 minutes. Afterwards, the cell-containing gels are crushed into small particles and washed with physiological saline to obtain 100 parts of the immobilized cells.

Five jacketed columns, 3 cm inside diameter, 25 cm length, are each filled with 40 g of the immobilized cells and connected to each other in series. A 1.0% to 4.5% acrylonitrile aqueous solution is allowed to flow down via the top of column one at 22° C. to 60° C. at a flow rate of 25 to 100 ml/hr. Thereafter, 100 parts of the eluate are mixed with 4.5 parts of acrylonitrile, and allowed to flow down from the top of column two at the same temperature and similar flow rate as column one. The eluate is collected and then applied to the top of column three and allowed to flow down column three at the same temperature and similar flow rate as column two. The eluate is collected and applied to the top of column four and allowed to flow down column four at the same temperature and similar flow rate as column three. The eluate is collected and then applied to the top of column five and allowed to flow down column five at the same temperature and similar flow rate as column four. The eluate is collected and the amount of acrylamide is determined as in Example 1.

EXAMPLE 6

The nitrile hydratase enzyme of BR449 is purified according to the procedure set forth below. This purification method is only an example and is not intended to imply that it is the only method for purifying the nitrile hydratase of BR449.

Bacillus sp. BR449 (ATCC 202119) is grown in OP medium at pH 7.2 which contained per liter: $KH_2PO_4$, 1 g; $K_2HPO_4$, 0.5 g; yeast extract, 1 g; malt extract, 1 g; peptone 2 g; glycerol, 3 g; casamino acids, 0.1 g. The isolate is grown at 60° C. using turbidity to monitor culture density. $Co^{2+}$ is added to the growth medium at a concentration of 20 mg/l.

The BR449 cells are collected by centrifugation at 10,000×g for 10 minutes. After washing, the cells are resuspended in 300 ml of 50 mM HEPES-KOH buffer. PH 7.2, and disrupted with a French press at 20,000 psi. The cell debris and undisrupted cells are removed by centrifugation at 10,000×g for 30 minutes. The supernatant fraction is dialysed against four changes of 10 mM HEPES-KOH buffer, pH 7.2, at 4° C. for 24 hours. Afterwards, the dialysate is passed through an anion exchange column containing DEAE-Sepharose FF (Pharmacia, Piscataway, N.J.) resin equilibrated with 50 mM HEPES-KOH, pH 7.2. The nitrile hydrase is allowed to be adsorbed by the column resin. The column is then washed with 50 mM HEPES-KOH, pH 7.2, to remove unbound material. Then the column is eluted using a 0.0 M to 1.0 M potassium chloride gradient of 50 mM HEPES-KOH, pH7.2. Elution fractions are analyzed for nitrile hydratase activity as set forth below. Those fractions containing nitrile hydratase are pooled and dialyzed against four changes of 10 mM HEPES-KOH buffer, pH 7.2, at 4° C. for 24 hours. The dialyzate is further purified by anion chromatography as above except that the potassium chloride gradient is from 0.2 M to 0.8 M. The fractions containing nitrile hydratase activity as set forth below are pooled and dialyzed as above. This results in a crude enzyme preparation enriched for nitrile hydratase activity.

To test enzyme preparations for nitrile hydratase activity, 0.1 ml of the crude enzyme solution is added to 1.0 ml of 0.5M acrylonitrile and potassium phosphate buffer, containing 0.5M acrylonitrile, pH 7.5. The reaction mixture is incubated in a water bath at 50° C. with shaking for 10 minutes, and the reaction is stopped by addition of 0.2 ml 2N HCl. Acrylamide formation is measured using HPLC by injection into a Novapak C-18 reverse phase column and eluted with 1:12 acetonitrile:5 mM potassium phosphate buffer, pH 2.5. Peaks are identified at 200 nm with a Waters (Newton, Mass.) variable wavelength detector and analyzed with reference to chemical standards. One unit of nitrile hydratase activity, is defined as the formation of one micromole acrylamide per minute. Amidase activity is measured in the same manner using 0.5M acrylamide as substrate by measurement of acrylic acid formation.

EXAMPLE 7

This Example is to determine whether the nitrile hydratase of BR449 can convert other nitrile compounds to its corresponding amide.

Examples of other nitrile compounds that can be converted into its corresponding amide compounds according to the present invention are aliphatic nitrites such as n-butyronitrile, n-valeronitrile, isobutyronitrile, acetonitrile and pivalonitrile; halogen-containing nitrile compounds such as 2-chloropropionitrile; unsaturated aliphatic nitrile compounds such as crotononitrile and methacrylonitrile; hydroxynitrile compounds such as lactonitrile and mendelonitrile; aminonitrile compounds such as 2-phenylglycinonitrile; aromatic nitrile compounds such as benzonitrile and cyanopyridines; and dinitrile compounds such as malononitrile, succinonitrile and adiponitrile.

Bacillus sp. BR449 (ATCC 202119) is grown in DP medium at pH 7.2 which contained per liter: $KH_2PO_4$, 1 g; $K_2HPO_4$, 0.5g; yeast extract, 1 g; malt extract, 1 g; peptone 2 g; glycerol, 3 g; casamino acids, 0.1 g. The isolate is grown at 60° C. using turbidity to monitor culture density. $Co^{2+}$ is added to the growth medium at a concentration of 20 mg/l.

Nitrile hydratase activity is measured using whole cells in assays containing 20 mg (dry wt) cells, in 1 ml 0.5M acrylonitrile and potassium phosphate buffer, containing 0.5M of the appropriate nitrile, pH 7.5. The reaction mixture is incubated in a water bath at 50° C. with shaking for 10 minutes, and the reaction is stopped by addition of 0.2 ml 2N HCl. Amide formation is measured using HPLC by injection into a Novapak C-18 reverse phase column and elution with 1:12 acetonitrile: 5 mM potassium phosphate buffer, pH 2.5. Peaks were are identified at 200 nm with a Waters (Newton, Mass.) variable wavelength detector and are analyzed with reference to chemical standards.

Rate of amide production from each nitrile compound at various temperatures is determined by incubating BR449 cells grown as above with shaking in 2% of the nitrile compound, 50 mM phosphate buffer, pH 7.5.

EXAMPLE 8

This example describes the DNA cloning and sequencing of the nitrile hydratase and amidase genes from BR449. FIG. 10 shows the region of the BR449 genome that was subcloned into plasmids for DNA sequencing. The cloning and sequencing was performed according to the procedures in Sambrook et al (*Molecular Cloning: A Laboratory Manual*, Cold Spring Harbor Laboratory, Cold Spring Harbor, N.Y. (1989)). The plasmids were commercially available. The DNA region was shown by sequencing analysis to encode the alpha and beta subunits of the nitrile hydratase gene. The region was also found to encode a gene with amidase activity and an open reading frame with unknown activity which was designated as ORF 1.

EXAMPLE 9

This example shows that a DNA fragment containing the nitrile hydratase gene conferred hydratase activity on *Escherichia coli* DH5α transformed with the DNA fragment. The nitrile hydratase activity was found to need cobalt and low temperatures for maximum activity. However, the cloned nitrile hydratase gene was found to be much better that other nitrile hydratase genes cloned into *E. coli* such as the nitrile hydratase gene from Rhodococcus.

Briefly, to make the recombinant *E. coli*, a 2,645 bp PstI/SalI DNA fragment (FIG. 20) containing part of the amidase gene, the beta and alpha subunits of the nitrile hydratase gene and ORF 1 was cloned into *E. coli* DH5α using standard molecular biology techniques as disclosed by Sambrook et al in: *Molecular Cloning: A Laboratory Manual*, Cold Spring Harbor Laboratory, Cold Spring Harbor, N.Y. (1989). The nitrile hydratase activity was measured according to the assays in Example 1. This PstI/SalI DNA fragment conferred nitrile hydratase activity to the recombinant *E. coli* which in was active in the presence of cobalt ions and at low temperatures. The above methods are used to clone the amidase and ORF 1 genes into *E. coli* to express their respective gene products.

EXAMPLE 10

Expression vectors and transforming bacteria, yeast, and plants with the nitrile hydratase, amidase, and/or ORF 1 genes. As an example, the nitrile hydratase gene is cloned into an expression vector which is operably linked to a promoter at the 5' end of the gene. For expression in procaryote cells, a DNA fragment containing the beta and alpha subunits in tandem is operably linked to the 5' end of the beta subunit to produce a polycistronic mRNA which is translated into separate alpha and beta subunits. One promoter for expression of both the alpha and beta subunits is sufficient because each gene of a polycistronic MRNA is normally translated in procaryotes. However, in eukaryotes, the second coding region of a mRNA is not normally translated. Therefore, for expression of both the beta and alpha subunits in eukaryotes, the 5' end of DNA fragments, each encoding one of the subunits is each operably linked to a promoter. Thus, expression of each subunit is separate or independent of the other. An example of a eukaryote that is useful for expression of nitrile hydratase, amidase, and/or ORF 1 is yeast. Other eukaryotes that are useful for expressing the nitrile hydratase include plants.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the Claims attached herein.

We claim:

1. A process for conversion of an amide to the corresponding carboxylic acid comprising:
   (a) contacting the amide with an amidase isolated from a thermophilic Bacillus sp. deposited as ATCC 202119; and
   (b) isolating the acid produced.

2. The process of claim 1 wherein the amide is acrylamide and the acid is acrylic acid.

3. A process for conversion of an amide to the corresponding carboxylic acid comprising:
   (a) contacting the amide with a thermophilic Bacillus sp. deposited as ATCC 202119; and
   (b) isolating the acid produced.

4. The process of claim 3 wherein the amide is acrylamide and the acid is acrylic acid.

5. The process of claims 3 or 4 wherein the Bacillus sp. is cultured with a divalent metal salt.

6. The process of claims 3 or 4 wherein the Bacillus sp. is cultured with $CO^{+2}$ ions.

* * * * *

UNITED STATES PATENT AND TRADEMARK OFFICE
CERTIFICATE OF CORRECTION

PATENT NO. : 6,287,828 B1
DATED : September 11, 2001
INVENTOR(S) : Patrick J. Oriel, Rugmini Padmakumar and Sang Hoon Kim It is certified that error appears in the above-identified patent and that said Letters Patent is hereby corrected as shown below:

Column 2,
Line 66, the period "." after "amide" and before "from" should be deleted.

Column 4,
Line 20, "and $\Delta 22°C$" should be -- ▲22°C --.

Column 8,
Line 12, "(b) isolating the" should be -- (d) isolating the --.

Column 9,
Line 24, "genes can constructed" should be -- genes can be constructed --.

Column 11,
Line 64, "unlike the in BR449" should be -- unlike in the BR449 --.

Column 12,
Line 25, "NHCl, 1g; MgSQ" should be -- $NH_4Cl$, 1g; $MgSO_4$ --.

Column 14,
Line 9, "of 10o %" should be -- of 10% --.

Column 14, Table 2,
Lines 9, 10, 12, 19, 22, 24, 28, 29, 30 and 32, "165" should be -- 16S --.
Line 13, "*Baciilus caldoveiox*" should be -- *Bacillus caldovelox* --.
Line 14, "emb | Z26923 | BT16SRRNB" should be -- emb | Z26923 | BT16SRRNF --.
Line 15, "*Baciilus caidolyticus*" should be -- *Bacillus caldolyticus*".
Line 17, "BKAU165R" should be --BKAU16SR --
Line 20, "gb | N77" should be -- gb | M77; and "*Bacilius thermodenitrificans*" should be -- *Bacillus thermodenitrificans* --.
Line 28, "AB095 165" should be -- AB005 16S --.

Column 15, Table 2,
Line 4, "165" should be -- 16S --.
Line 5, "emb | X6446S | BM16SRRN" should be -- emb | X64465 | BM16SRRN --.
Line 6, "eeb | X60643 | B8M1168R" should be -- emb | X60643 | BSMI16SR --.
Line 8, "dbj | D2618S | " should be -- dbj | D26185 | --.
Line 9, "165" should be -- 16S --.
Line 10, "with 235" should read -- with 23S --.
Line 11, "94558 | HL | 6SRRN1 *H. litoraiis* 16S" should be -- 94558 | HL16SRRN1 *H. litoralis* 16S --.

UNITED STATES PATENT AND TRADEMARK OFFICE
CERTIFICATE OF CORRECTION

PATENT NO.    : 6,287,828 B1
DATED         : September 11, 2001
INVENTOR(S)   : Patrick J. Oriel, Rugmini Padmakumar and Sang Hoon Kim It is certified that error appears in the above-identified patent and that said Letters Patent is hereby corrected as shown below:

Column 17,
Line 53, "shows that" should be -- shows there --.

Column 19,
Line 62, "The dialyzate" should be -- The dialysate --.

Column 20,
Line 24, "nitrites" should be -- nitriles --.

Column 21,
Line 13, "that other" should be -- than other --.
Line 26, "which in was active" should be -- which was active --.

Signed and Sealed this

Seventh Day of May 2002

Attest:

Attesting Officer

JAMES E. ROGAN
Director of the United States Patent and Trademark Office